United States Patent [19]
Cresswell et al.

[11] 3,991,050
[45] Nov. 9, 1976

[54] PREPARATION OF β-AMINO-α-BENZYLACRYLONITRILES

[75] Inventors: Ronald M. Cresswell, Raleigh; John W. Mentha, Washington, both of N.C.

[73] Assignee: Burroughs Wellcome Co., Research Triangle Park, N.C.

[22] Filed: June 18, 1975

[21] Appl. No.: 587,868

Related U.S. Application Data

[60] Continuation of Ser. No. 278,993, Aug. 9, 1972, abandoned, which is a division of Ser. No. 75,276, Sept. 24, 1970, which is a continuation-in-part of Ser. No. 16,605, March 4, 1970, abandoned.

[30] Foreign Application Priority Data

Mar. 6, 1969    United Kingdom............... 11908/69
Mar. 6, 1969    United Kingdom............... 11909/69
May 16, 1969    United Kingdom............... 25171/69
June 13, 1969    United Kingdom............... 30247/69

[52] U.S. Cl............................ 260/240 R; 260/340.5; 260/465 E
[51] Int. Cl.²............... C07D 295/00; C07D 317/06; C07C 121/78
[58] Field of Search .......... 260/465 E, 240 R, 340.5

[56] References Cited
FOREIGN PATENTS OR APPLICATIONS
957,797    5/1964    United Kingdom

*Primary Examiner*—Lewis Gotts
*Assistant Examiner*—Dolph H. Torrence
*Attorney, Agent, or Firm*—Donald Brown

[57]      ABSTRACT

Compounds and methods of making compounds of the formula

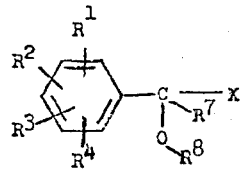

Where X is a diloweralkylsulphone or diloweralkyl sulphoxide group and $R^1$–$R^4$ is hydrogen, loweralkyl, loweralkoxyl, halogen, benzyloxy or methylenedioxy provided that one of $R^1$–$R^4$ is a substituent other than hydrogen, and where $R^7$ and $R^8$ are hydrogen atoms or together represent an additional bond between the carbon and oxygen atoms. The compounds are useful as intermediates in the method of preparing other valuable intermediates which are useful in preparing antibacterial agents.

33 Claims, No Drawings

PREPARATION OF β-AMINO-α-BENZYLACRYLONITRILES

This is a continuation of application Ser. No. 278,993 filed on Aug. 9, 1972, now abandoned, which is a division of U.S. Ser. No. 75,276 filed Sept. 24, 1970 which is a continuation-in-part of Ser. No. 16,605 filed Mar. 4, 1970.

This invention relates to improved methods of preparing 5-benzylpyrimidines and more particularly is related to a class of stable α-benzylacrylonitrile intermediates, and to methods of making such compounds.

2,4,-Diamino-5-benzylpyrimidines possess both antimalarial and antibacterial activities (J. Am. Chem. Soc., 1951, 73, 3758). Maximal antibacterial activity is found among derivatives which bear electron donating substituents in the benzene nucleus and are unsubstituted in the 6th position of the pyrimidine moiety. 2,4-Diamino-5-(3',4',5'-trimethoxybenzyl)pyrimidine or trimethoprim (U.S. Pat. No. 2,909,522) has a moderately broad antibacterial spectrum which includes many of the Gram-positive species but it is also active against species of the genus Proteus. In common with other 2,4-diaminopyrimidines it is a competitor of folic and folinic acids in microorganisms which require these nutrilites, and it can be shown to inhibit dihydrofolate reductase in Streptococcus faecalis. A strong potentiative effect is observed when the drug is administered in combination with sulphonamides as a consequence of the sequential blockade of the biochemical pathway which leads to the de novo synthesis of coenzymes F. This potentiation may be demonstrated both in vitro and in experimental infections in mice with Staphylococcus and Proteus species.

2,4-Diamino-5-benzylpyrimidines, which includes trimethoprim and 2,4-diamino-5-(3,4'-dimethoxybenzyl)pyrimidine or diaveridine and 2,4-diamino-5-(3',-4'-dimethoxy-5-bromobenzyl)pyrimidine (U.S. Pat. No. 2,658,897), may be administered orally at a dose of 1 mg/kg to 30 mg/kg per day.

Preferably these compounds are administered in tablet form to a mammal being treated, and trimethoprim may advantageously be combined with sulphamethoxazole against certain respiratory infections. A further example of this class is 2,4-diamino-5-(2'-methyl-4',5'-dimethoxybenzyl)pyrimidine (ormetoprim), which has been reported to show antibacterial activity, and also has coccidiostatic properties when combined with sulphadimethoxine.

A new route was developed some years ago for the preparation of 2,4-diamino-5-benzylpyrimidines (see Stenbuck, Baltzly and Hood, J. Org. Chem., 1963, 28, 1983 and British Pat. Specification No. 957,797). This route comprises the steps of (i) condensing an aromatic aldehyde with a β-substituted propionitrile in the presence of both an alcohol as solvent and a strong base to give a mixture of isomers of formulae (Ia) and (Ib) respectively:

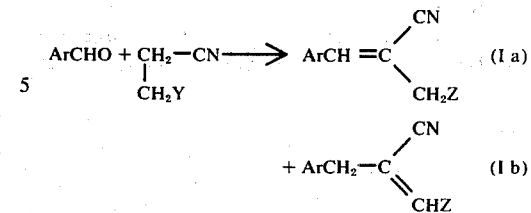

wherein Ar is an optionally substituted phenyl group, Y is an alkoxy, thioalkyl or dialkylamino group, and Z is the group Y or is an alkoxy group derived from the solvent alcohol; and (ii) reacting either the pure 'benzal' isomer (Ia) or a mixture of 'benzal' and 'benzyl' isomers (Ia) and (Ib) respectively with guanidine to give a 5-benzylpyrimidine of formula

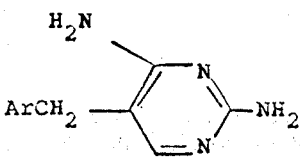

Although it was known that the intermediate product obtained in the first step was a mixture of isomers of formulae (Ia) and (b), only the (Ia) 'benzal' isomer could be isolated in a crystalline form after some purification steps. The two isomers were assumed to be in equilibrium with each other when prepared under alkaline conditions and further reacted with guanidine according to the aforesaid disclosures, but it was not clearly established which of the isomers was primarily interacting in the second step. In many cases this method affords acceptable yields but in certain instances extensive losses (up to about half the material used) ensue from formation of yellow polymers.

The further conversion of composite mixtures of derivatives and isomers according to British Pat. Specification No. 957,797, afforded the required 2,4-diamino-5-benzyl-pyrimidines only in yields between 25 and 45%, and in view of the importance of the final products and the difficulties with by-products and impurities, alternative methods were also explored by various investigators. For instance, a prior written document discloses a process comprising the steps of (a) reacting acetylthymine with N-bromosuccinimide to form acetylbromothymine, (b) condensing the product with a substituted benzene, (c) reacting the product with a halogenating agent, and (d) aminating the halogeno derivative. However, this process suffers from the disadvantages that acetylbromothymine is expensive to make, condensation with the benzene compound does not provide the further intermediate in a high yield, and the last stage requires operation under pressure and usually results in an equilibrium state with consequent poor yields. Altogether the process requires four stages to obtain the final product, and none of the stages is particularly advantageous.

Subsequent developments showed that the polymer formation obtained when operating the process described in the specification of British Patent No. 957,797, could be prevented or reduced in cases of β-alkoxy-derivatives of compounds (Ia) and (Ib) by temporarily saturating the double bond with excess alkoxide in alcohol.

This provides the corresponding acetal of formula (II), for instance, according to the reaction outlined below:

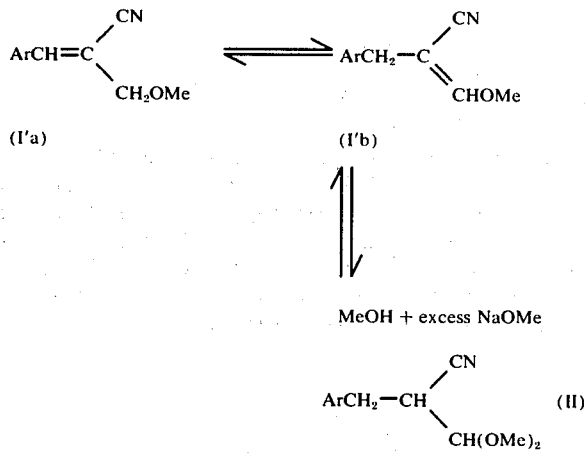

When the acetal (II) is subsequently treated with guanidine in alcoholic solution, the alkaline condition is thought to catalyse the reconstitution of the double bond, initially in the form of (I'b), and the intermediate can thus react with guanidine to give the desired 5-benzylpyrimidine.

Acetals of formula (II) may also be prepared by condensing the corresponding aromatic aldehyde with a 3,3-dialkoxy-propionitrile and reducing, preferably catalytically, the 3,3-dialkoxy-2-benzalpropionitrile intermediate so obtained. (See U.S. Pat. No. 3,487,083).

The aforesaid British Patent Specification No. 957,797 also describes (Example 14) the reaction of veratraldehyde with β-dimethylaminopropionitrile in the presence of sodium in ethanol to give a mixture of β-dimethylaminoveratralnitrile (III) and β-ethoxyveratralnitrile (IV) in a 32% yield.

can be prepared remarkably readily under a conveniently wide variety of conditions and that the products so obtained are not only substantially free of contamination with the corresponding benzal isomer but manifest an unexpected stability and capability of maintaining their configuration.

The 'benzyl' configuration of these compounds shows little or no tendency to isomerise into the benzal form prepared and exemplified in the British Pat. Specification No. 957,797. Furthermore, the β-amino-α-benzylacrylonitriles can be converted into benzylpyrimidines or into other benzyl derivatives, which may be used as preferred for the preparation of benzylpyrimidines or other heterocyclic ring systems.

According to the present invention in one aspect therefore there is provided an N-substituted-β-amino-α-benzylacrylonitrile compound of the formula (V), in a form substantially free from contamination with the β-amino-α-benzylidenepropionitrile isomer. In particular the contamination with the benzal isomer is normally substantially below 10%, taken as a percentage of the amount of compound of formula (V), and preferably below 5 or, still better, below 2%. Usually the best methods for making the compound of formula (V) provide the product with less than 0.5% contamination and frequently no benzal isomer can be detected at all with analytical methods sensitive to even as low as 0.33% admixture. It has, on the other hand, been observed that contamination at or above the 10% level adversely affects the yield and quality of the final benzylpyrimidine product, and the appearance of purple or yellow discolourisation may aggravate the difficulties, especially isolation in a pure form, an essential requirement when the product is to be used clinically, there therefore being necessary many tedious, time-consuming and accordingly expensive purification steps.

As previously defined Ar is an optionally substituted phenyl group in formula (V). The β-amino group $NR^5R^6$ is an aliphatic, heterocyclic or aromatic amino group, and can have only one hydrogen atom for $R^5$ and $R^6$. In general it may be stated that, as a free amine,

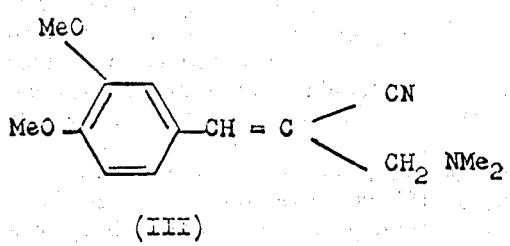

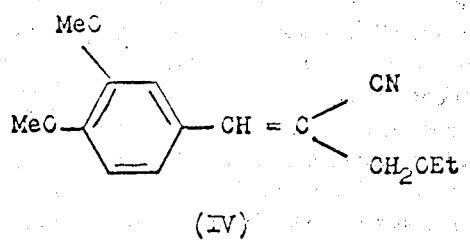

It is stated in the Example that this mixture was subsequently cyclised with guanidine to give 2,4-diamino-5-(3',4'-dimethoxybenzyl)-pyrimidine. It is to be noted that both the compounds (III) and (IV) above are benzal derivatives.

It has now been found that N-substituted β-amino-α-benzylacrylonitriles of the configuration of formula (V)

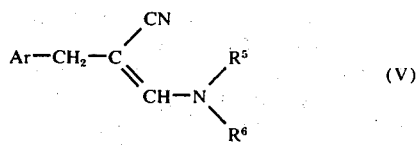

$HNR^5R^6$ is preferred to have a pKa value not lower than about 0, and also most preferably not higher than about 6.

In particular, it is especially preferred that the $NR^5R^6$ group is a primary anilino group (e.g. aniline, o and p-toluidine p-anisidine, p-chloroaniline, 2,5 and 3,4-dichloroanilines). The phenyl ring of this group may be optionally substituted with one or more substituents such as halogen atoms, and alkyl and alkoxy groups, but the unsubstituted anilino group is, however, particularly preferred.

The $NR^5R^6$ group may also be a primary amino group other than the aforesaid primary anilino group, such as a monoalkylamino, benzylamino, or naphthylamino, preferably α-β-naphthylamino group; or may be a secondary amino group, such as a dialkylamino, N-ethylanilino pyrrolidino, piperidino, N-methylanilino or a piperazino group, or most preferably the morpholino group.

In particular the invention provides compounds of formula (VIII), in a form substantially free from contamination with the β-amino-4-benzylidene-propionitrile isomer, as hereinbefore defined:

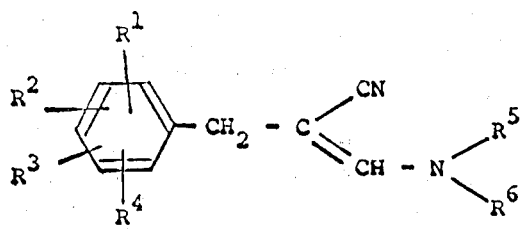

(VIII)

wherein the group —NR$^5$R$^6$ is as hereinbefore defined with reference to a compound of formula (V), and R$^1$, R$^2$, R$^3$ and R$^4$ are the same or different and each is a hydrogen or a halogen atom, an alkyl, alkoxy, or benzyloxy group, or R$^3$ and R$^4$ taken together may be a methylenedioxy group when both R$^1$ and R$^2$ are hydrogen atoms. Preferably the whole amino group NR$^5$R$^6$ comprises not more than 12 carbon atoms.

All of the above compounds of formula VIII are convertible to benzyl pyrimidines and such pyrimidines are useful as antibacterials.

In formulae (V) and (VIII), and elsewhere in this application each of the alkyl or alkoxy groups in the substituents may have from 1 to 4 carbon atoms, e.g. they may be methyl, ethyl, propyl or butyl groups, including normal, iso or tertiary branched forms, and corresponding alkoxy groups. Each of the halogen atoms may be represented by a chlorine, bromine, fluorine or iodine atom.

More particularly the para-position of the phenyl group may be substituted with a benzyloxy, but preferably an alkoxy group, such as a methoxy group, especially with a similar or identical alkoxy substitution at one or advantageously both adjacent positions on the phenyl ring. As another possibility alkoxy, e.g. methoxy substitution, in such positions may be combined with an alkyl, e.g. methyl, substitution at the ortho-position of the phenyl group.

The compounds of formulae V (or VIII) fall into two classes VIII A and B dependent on their reactivity towards guanidine.

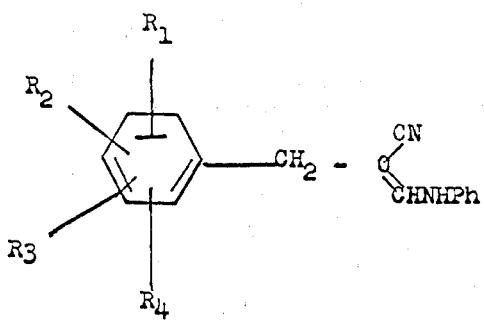

VIII A

Wherein Ph is an aryl group of 6 to 12 carbon atoms which may be substituted in one, two, or three positions with lower alkyl, lower alkoxyl, and halogen, preferably chlorine and where the R$_1$ – R$_4$ are defined as previously and lower alkyl halogen and lower alkoxyl are as previously defined. Compounds of type VIII A react readily with guanidine in e.g. solvent lower alcohol solution to form 2,4-diamino-5-benzylpyrimidines in good yield. Advantageously the reaction is conducted at the reflux temperature of the solution, but useful rates are found at lower temperatures down to room temperatures. These compounds are consequently preferred.

The compounds of formula VIII B wherein R$_5$ is alkyl or aryl and R$^6$ is alkyl and may also be hydrogen when R$_5$ is alkyl and NR$_5$-R$_6$

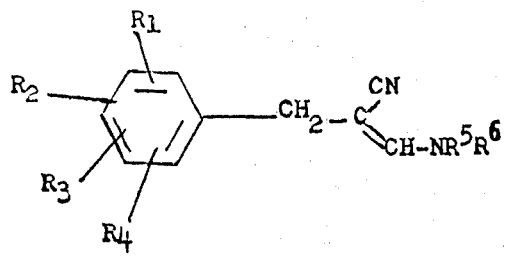

VIII B may also be cyclic amino such as morpholino, piperidino and pyrrolidino, react only slowly with guanidine base, so that periods of 1–2 weeks would be required for complete reaction. They can be converted to pyrimidines by reaction with guanidine carbonate in a polar aprotic solvent (as defined below but preferably DMSO) at an elevated temperature. This reaction is slow below 140° C but goes rapidly at about 160° C or above.

The compounds according to formula (V) or (VIII), respectively, may be prepared by a wide variety of methods. The actual choice between these methods in any particular instance depends primarily on the reactivity of the compound obtained, and the further processing to which it may be subjected to provide compounds such as pyrimidines of clinical utility, the further processing being itself governed to a great extent by the nature of the amino group NR$^5$R$^6$, this acting as a leaving group in the further reactions.

Compounds according to formula (V) or (VIII) can be prepared by a method provided by the present invention, which comprises reacting the corresponding benzaldehyde with the corresponding β-aminopropionitrile in the presence of a base in a polar aprotic solvent compatible with and dissolving both reactants.

Polar aprotic solvents suitable for the purpose include hexamethylphosphoramide and N,N-dimethylacetamide, but best results have been obtained with dimethylsulphoxide as the solvent. Bases required for the reaction include the hydroxide, the alkoxides, especially the lower alkoxides, preferably the methoxide or tert.-butoxide anions, and the methylsulphinyl carbanion, used in association with a suitable cation, such as an alkali metal (e.g. sodium or potassium) or a quaternary ammonium cation (e.g. N-benzyl-N,N,N-trimethylammonium).

Advantageously, the amount of base can be considerably reduced to "catalytic amounts", i.e. effective quantities of less than about 0.3 molar equivalent calculated on the aldehyde used, particularly at temperatures above 60° C, preferably between 90° C and 130° C. For instance, very good yields have been obtained in this manner using dimethylsulphoxide as the solvent.

Very satisfactory yields have also been obtained, for instance, with β-primary anilino-substituted compounds with 0.5 to 2 molar equivalents of the base at room (about 20° C) or slightly elevated temperature up to about 60° C in the solvent. Dimethylsulphoxide may be replaced under these conditions as well as by other polar aprotic solvents, especially hexamethylphosphoramide. It has been found most advantageous to use t-butoxide as the base in the form of the potassium salt in dimethylsulphoxide for the preparation of β-anilino-substituted compounds whilst, for instance, the β-morpholino-analogue may be preferred to be formed in the presence of sodium methoxide in the same medium.

Yet further methods provided by the present invention may be used to obtain selected or preferred ranges of compounds within the scope of formula (V) or (VIII). Accordingly, a method is provided for preparing such compounds, wherein the β-amino group $NR^5R^6$ is a primary anilino group optionally substituted in the phenyl ring, as hereinbefore defined, which comprises reacting the corresponding benzaldehyde with the corresponding β-primary-anilino-propionitrile. Preferably the reaction is carried out in a polar non-aprotic solvent compatible with and dissolving the reactants in the presence of a base. Conveniently an alkanol may be used for the purpose, and the reaction is desirably carried out at elevated temperatures, say between 40° and 80° C. The preferred alkanol is methanol, particularly when the reactant benzaldehyde is substituted with one or more methoxy groups, since it is possible for exchange to take place between the solvent and the substituents. Bases already listed in relation to the other preparatory methods are again applicable, and may, for instance, be used in a quantity molar equivalent calculated on the aldehyde, especially when the reaction is carried out at the lower end of the indicated temperature range.

Compounds according to formula (V) or (VIII) can also be prepared by reacting the corresponding β-hydroxy-β-phenethylmethylsulphone or sulphoxide with the corresponding β-amino-propionitrile. Very preferably the reactions carried out in the presence of a base in a polar non-aqueous solvent compatible with and dissolving both reactants of elevated temperature above 30° C. The solvent may be an alkanol, such as methanol, ethanol or isopropanol, or most conveniently a polar aprotic solvent such as exemplified above. The base is preferably sufficiently strong on its own for a significant amount of the sulphone or sulphoxide reactant to be converted into the anionic form. Again hydroxides or alkoxides, preferably methoxide or t-butoxide, in the form of an alkali metal salt, have been found very convenient for the purpose. The method is especially suitable for making Type VIII A.

The required β-hydroxy-β-phenethyl methylsulphone or sulphoxide for the above method, may conveniently be provided by a process which comprises the steps of reacting an appropriately substituted benzoic acid ester with dimethyl sulphone or dimethyl sulphoxide preferably in the presence of a base, and selectively reducing the so obtained acetophenone methylsulphone or methylsulphinyl derivative, for instance, with a suitable reducing agent, e.g. (borohydride or with aluminium isopropoxide).

More particularly it has not been found that the compounds of formula IX found later in the specification may be obtained very readily with numerous particular advantages by the reaction sequence shown in the flow sheet on page 20A hereof, which discloses by way of example only, the sequence to obtain the compound trimethoprim but is equally applicable to the compounds of the general formula IX.

Compound (XI) is the readily available gallic acid;
Step (i) and (ii) are known literature methylations;
Step (iii) involves reaction with dimethyl sulphone;
Step (iv) is a reduction;
Step (v) is a reaction with a β-amino substituted-propionitrile as previously defined, i.e. with

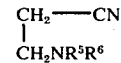

as previously defined.

Compound (XII) is a β-Z-substituted-α-benzylacrylo-nitrile where Z is $NR^5R^6$ as previously defined.

The compound (XII) is then reacted with guanidine to prepare the corresponding benzyl pyrimidine (e.g. trimethoprim) which are useful as antibacterials.

The dimethyl sulphone $CH_3.SO_2.CH_3$ used in step (iii) may be replaced by dimethyl sulphoxide $CH_3.SO.CH_3$. though dimethyl sulphone is the most advantageous reagent so far found.

It has also been found that the above reactions are generally applicable. Thus $R^1 - R^4$ substituted-benzoic esters, where $R^1 - R^4$ are as previously defined with reference to compound VIII react readily with dimethyl sulphone or dimethyl sulphoxide according to the reaction (a):

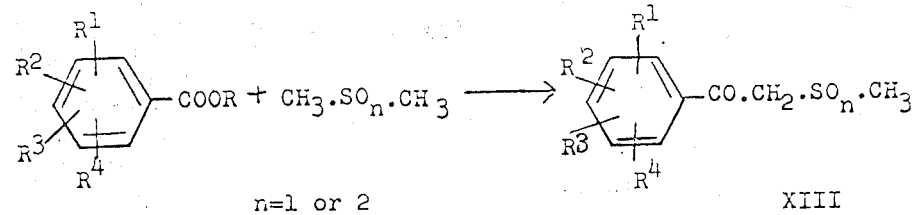

n=1 or 2

XIII

R is alkyl (e.g. methyl, ethyl, propyl, butyl,) preferably 1 to 4 carbons.

Furthermore, the compounds of formula XIII are readily reduced according to the reaction (b):

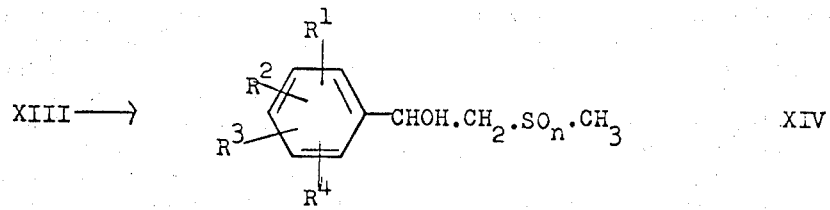

wherein $R^1$–$R^4$ and $n$ are each as defined above. The compounds of formula XIV react readily with β-Z-substituted-propionitriles according to the reaction (c):

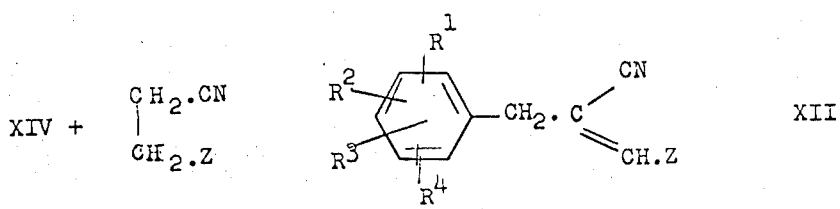

wherein $R^1$ – $R^4$ and Z are each as defined above.

In the reactions described in the present specification, it is preferred that the phenyl group is substituted with an alkoxy group, especially methoxy group, in the para or meta position, and most advantageously in both or all such positions. The alkyl or alkoxy groups defined in the above formulae include normal, iso or tertiary branched forms. According to the present invention, valuable intermediates of Formula XV are provided, particularly where at least one of $R^1$ - $R^4$ is a substituent other than hydrogen.

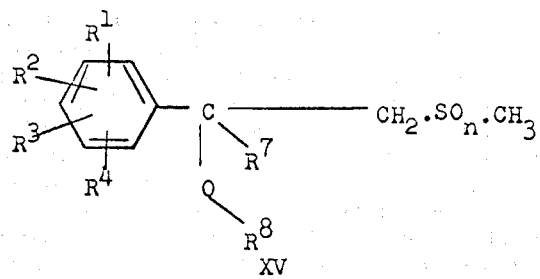

and generally, wherein $R^1$ – $R^4$ and $n$ are each as defined above, or previously herein, and $R^7$ and $R^8$ are hydrogen atoms or together represent an additional bond between the carbon and oxygen atoms. In a particular aspect, such compounds have an alkoxy substituent in the para position of the phenyl group, and preferably carry such substitutions in both or all para and meta positions.

The reaction of a benzoic ester as exemplified by step (iii) in the reaction sequence in the accompanying flow sheet (page 25) and reaction (a) above, is effected in the presence of a base, which for best results is used in conjunction with dimethyl sulphoxide as the solvent. Desirably the two are mixed prior to the addition of the benzoic ester. Any base sufficiently strong to provide the methylsulphinyl or methylsulphonyl carbanion in an adequate quantity is suitable for the reaction. Preferably the reaction is carried out in a solvent with the base supplied as sodamide or sodium hydride, from which ammonium or hydrogen are released with a complete conversion to the above mentioned anions.

The reduction exemplified by step (iv) and reaction (b) may conveniently be effected by using a reducing agent reacting in solution, i.e. in a homogeneous system. Conveniently complex hydrides, such as those of boron or aluminium compatible with alcoholic or aqueous solvents may be employed for instance in the form of a suitable alkali metal, e.g., sodium or lithium, salt. Other types of reducing agents, such as aluminium isopropoxide in isopropanol, may also be used for the purpose. Preferably the reducing agent will not reduce the sulphone or sulphoxide group in the compounds of steps (IV) and (V).

The reaction with a β-Z-substituted-propionitrile exemplified by step (V) and reaction (c) is most advantageously performed in the presence of both a base and a solvent. The base is desirably a hydroxide or alkoxide, preferably a methoxide or a tertiary butoxide ion, or the methylsulphinyl carbanion in a dimethyl sulphoxide medium, and is conveniently supplied in the form of an alkali metal (e.g. sodium or potassium) or quaternary (e.g.N-benzyl-N,N,N-trimethyl) ammonium hydroxide or alkoxide. The solvent is a polar non-aqueous solvent compatible with and dissolving both reactants. It may be an alkanol, such as methanol, ethanol or isopropanol, but most preferably a polar aprotic solvent, such as dimethyl sulphoxide, hexamethylphosphoramide or N,N-dimethylacetamide, is used. The propionitrile may be any of the compounds of the defined type disclosed in U.S. Pat. No. 3,049,544 and more particularly as disclosed herein.

The above defined group of β-primary-anilino-α-benzylacrylonitriles can also be prepared by a method which comprises reacting the corresponding aniline, generally in the form of an acid addition salt, with a compound of formula (V) or (VIII) carrying an amino substituent which has, as the free amine $HNR^5R^6$, a pKa value higher by at least about 3 to 4 units than that of the aniline used for the reaction. For instance, a morpholino substituent may, in this manner, be directly replaced by an anilino substituent, morpholine having a pKa value of about 8.6 and the aniline generally about 4 to 5. Preferably the reaction is carried in a polar non-aqueous solvent system, for instance, ethanol or glacial acetic acid, at reflux temperatures.

The compounds VIII A are also preparable by reaction of $PhNH_2$ with β-hydroxy-α-benzylacrylonitriles:

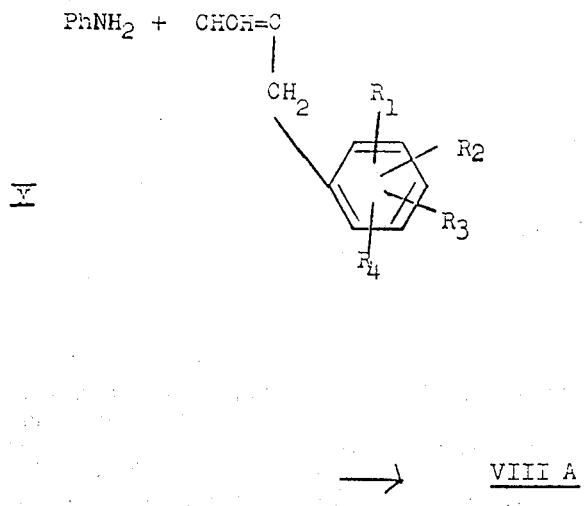

This reaction is conveniently carried out in an organic solvent such as benzene or a lower alcohol or without solvent, and where Ph is as previously defined or $PhNH_2$ could also be $NR^5 R^6$ where this is as previously defined.

The β-hydroxy-α-benzylacrylonitriles are prepared in exemplary fashion by acidification of a partly aqueous solution of a compound of type VIII B where $R_5$ and $R_6$ are not aromatic. For this variation in aqueous alcohol VIII B is converted to the hydroxy compound X almost instantaneously and in nearly quantitative yield.

The product may then be extracted with an organic solvent from the aqueous medium and reacted with a different amine to obtain a compound according to formula (V) or (VIII). There is little or no tendency to isomerize to the 'benzal' form during these manipulations.

Such a conversion from one amino derivative to another may be achieved in a very high yield, in many instances above 99% in both steps, and the product so obtained can be reacted to form other materials such as benzylpyrimidines in a quality and yield often even better than that provided by using the original β-amino-derivative.

In addition, this method may be very advantageous for preparing certain β-amino-α-benzylacrylonitriles, especially in cases where the $NR^5R^6$ group is basic but only weakly basic anilino group, e.g. p-chloro-anilino. In such instances, there are sometimes difficulties in preparing the corresponding β-anilino-propionionitrile for reaction with the benzaldehyde.

The β-hydroxy-α-benzylacrylonitriles may also be used as intermediates for further syntheses, and can, for instance, be alkylated to provide the appropriate β-alkoxy-α-benzylacrylonitrile, substantially free from the benzal isomer or acetal. The benzyl compound so formed and in such purity is also eminently suitable as a starting material for the synthesis of benzylpyrimidines, and provides the latter in a substantially increased yield and at a better quality than the mixture of benzyl and benzal isomers, or the benzal isomer alone, of the method described in British Pat. Specification No. 957,797.

Compounds according to formula (V) or (VIII), wherein the β-amino group $NR^5R^6$ is a primary amino group other than anilino, or is a secondary amino group, can also be prepared according to the present invention by reacting the corresponding β-alkoxy-α-benzylidenepropionitrile with an excess of the appropriate amine in the presence of a base in an alkanol. Suitable bases are again those already listed for other methods. Preferably the base is the alkoxide corresponding to the solvent. For instance, a β-methoxide-α-benzylidenepropionitrile may be so converted with morpholine, in methanol containing sodium methoxide, to the corresponding β-morpholino-α-benzylacrylonitrile.

The above group of compounds according to formula (V) or (VIII), wherein the β-amino-group $NR^5R^6$ is other than the anilino group, can moreover be prepared according to the present invention by isomerizing the corresponding β-amino-α-benzylidene-propionitrile isomer with a base in a polar aprotic solvent. Under these conditions the 'benzal' is isomerised into the benzyl form, there appearing to be little or no benzal isomer after the process. Suitable aprotic polar solvents and bases are as hereinbefore described with reference to other reactions, and the most preferred solvent is again dimethylsulphoxide and the most convenient bases are the methoxide and t-butoxide anions. Normally there is at least about 0.01, and preferably about 0.1 molar concentration of base present in the solvent, and often not more than about 1 molar concentration, though as high as 2 or even 4 molar concentrations may be used. The quantity of solvent is not critical though there is preferably sufficient throughout the isomerisation to dissolve the nitrile. The isomerisation can be effected at room temperature but is most conveniently carried out in the presence of heat, particularly good yields being obtained when it is carried out at a temperature above about 20° C. and up to about 75° C. or even higher. The method has been very successfully applied to β-morpholino-α-benzylidene-propionitriles, in particular to those having a 3,4-dimethoxy or 3,4,5-trimethoxy-benzylidene group.

The starting benzal isomer, i.e. the appropriate β-amino-α-benzylidene-propionitrile, for the purposes of the above reaction, can advantageously be prepared by reacting the corresponding benzaldehyde with the corresponding β-amino-propionitrile in an alkanol in the presence of a "catalytic amount" of a base, in the sense hereinbefore used in the present specification, which means an effective quantity of less than 0.3 molar equivalent calculated on the aldehyde reagent.

Alkanols in this reaction are generally lower alkanols, having from 1 to 4 carbon atoms, methanol being particularly preferred. Suitable bases are again those already suggested in connection with base catalysed condensation reactions, but methoxides and tert.-butoxides, particularly the former, are preferred for the present purpose. Best results may be obtained at elevated temperatures, and it is particularly preferred to carry out the reaction at reflux temperatures.

As already indicated, the optimum route for preparing any particular compound according to formula (V) or (VIII) may comprise a combination of a number of the above processing possibilities, depending primarily on the type of amino $NR^5R^6$ group required. For instance, β-primary-anilino-α-3',4',5'-trimethoxy-benzylacrylonitrile has certain especial advantages as an intermediate for the preparation of trimethoprim. Thus, the reaction of guanidine with β-primary-anilino-α-benzylacrylonitriles generally proceeds appreciably faster than that with other β-amino derivatives as defined by formula (V) or (VIII).

The β-anilino-intermediate can moreover be produced readily without any benzal isomer detectable by standard analytical methods, and can be further processed to 2,4-diamino-5-benzylpyrimidines in a very high yield there being little or no polymer formation at all. It is most noteworthy that the reaction with guanidine is readily effected under mild conditions, and both the preparation of the intermediate and the further processing may be completed within hours rather than weeks.

Whilst β-primary-anilino-α-benzylacrylonitriles may be readily prepared by a wide variety of advantageous methods, the choice in a particular instance depends partly upon the availability of the starting material, and, for instance, β-anilino-propionitrile, when prepared from aniline and acrylonitrile, usually requires isolation and purification before use. In contrast, the corresponding β-morpholino-propionitrile can be readily formed and need not be isolated. Furthermore, in cases of trimethoxy-substituted benzyl derivatives, and base catalysed reactions, the cheaper and more widely available sodium methoxide is preferred for morpholino-derivatives, whilst the more expensive potassium t-butoxide generally gives best results for anilino-compounds. It may therefore on occasion be advantageous to prepare the morpholino-intermediate first and convert this into the corresponding anilino derivative to obtain optimum results.

According to the present invention in a further aspect there is provided a method of preparing 2,4-diamino-5-benzylpyrimidines as shown in formula IX which are useful as antibacterials, wherein the benzyl group comprises an optionally substituted phenyl group, by reacting the corresponding β-amino-α-benzylacrylonitrile of formula (V), substantially free from contamination with the β-amino-α-benzylidene-propionitrile isomer, as hereinbefore defined, with guanidine. In particular a method is provided of preparing a compound of formula (IX)

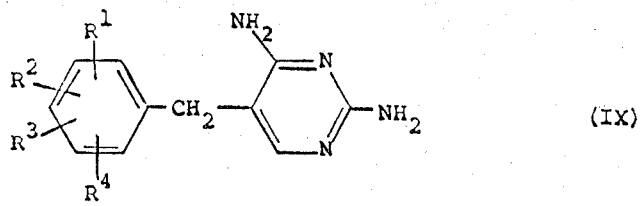

which comprises reacting a compound of formula (VIII) substantially free from contamination with the β-amino-α-benzylidenepropionitrile isomer, as hereinbefore defined, with guanidine; in formula (IX) $R^1$, $R^2$, $R^3$ and $R^4$ are as defined for formula (VIII). It has been found that the pyrimidine products are obtained in a satisfactorily high yield as well as without contamination with polymers and coloured impurities. These aspects are of critical importance as indicated hereinbefore, since contemporary requirements for the purity of pharmaceutical products are very stringent and the products must be manufactured in a very pure form and, of course, at a reasonable cost. Both these necessities are now more readily attainable, as a result of the present invention, for the benzylpyrimidines.

To obtain 5-benzylpyrimidines having particularly high activity, or potentiating properties, the para position of the phenyl group is preferably substituted with an alkoxy, i.e. methoxy group, especially in combination with a similar substitution at one or both adjacent meta positions. Such substitutions may also be present when at least one of the ortho-positions is occupied by a lower alkyl group, such as methyl. The pyrimidines are then trimethoprim, diaveridine, ormetoprim and analogues thereof.

For the purposes of obtaining 5-benzylpyrimidines or in particular those of formula (IX) preferably having the above mentioned specific substituents, the appropriate β-anilino-derivatives have been found particularly useful. Advantageously such an amine is reacted with guanidine, conveniently in a lower alcohol solvent, for example, methanol, ethanol, or isopropanol, at elevated temperatures. It is particularly preferred that the reaction is carried out at the reflux temperature of the reaction mixture, but useful routes are found at temperatures down to room temperatures. It has been found specifically that the reaction takes place very readily, taking hours rather than weeks for completion.

Although the reactivity with guanidine, of β-amino-α-benzylacrylonitriles of formula (V) or (VIII), other than those having a β-primary-anilino group, such as the morpholino derivatives is lower, particularly in alkanols, it has been found that this can be increased and the yield substantially improved if the guanidine is employed in the form of the carbonate in a polar aprotic solvent, as hereinbefore described with reference to other methods, e.g. especially dimethylsulphoxide or hexamethylphosphoramide. Best results have been obtained in these particular cases with dimethylsulphoxide at or near 160° C; and, if the previous reaction step has also been carried out in the same medium the β-amino-α-benzylacrylonitrile intermediate need not be isolated, although isolation is usually preferred since purer benzylpyrimidine is obtained in this manner.

All end products provided in the above manner have either antibacterial activity or potentiating properties, although the degree of such activity and potentiating effect may vary according to substitution and the purpose for which these compounds are employed. Moreover, the products may themselves be used as starting materials to produce other derivatives and analogues by further reactions with functional groups thereon. Thus benzyloxy-benzyl-derivatives may, for instance, be converted into the corresponding hydroxy-benzyl-derivatives by hydrogenation, or any hydroxy-benzyl-derivatives alkylated to provide the required alkoxy-benzyl-substituted compounds.

According to the present invention, there are provided:

i. N=substituted-β-amino-α-benzylacrylonitrile compounds according to formula (V), or, in particular, formula (VIII), substantially free from contamination with β-amino-α-benzylidenepropionitrile, as hereinbefore described;

ii. the various methods of preparing β-amino-α-benzylacrylonitriles of formula (V) or (VIII), as hereinbefore described;

iii. the various methods of converting such a β-amino-α-benzylacrylonitrile into a different compound of the same class with respect to the β-amino-substitution, as hereinbefore described;

iv. N-substituted β-amino-α-benzylacrylonitriles whenever prepared by a method defined under either of paragraphs (ii) and (iii), as hereinbefore described;

v. β-hydroxy-α-benzylacrylonitriles substantially free from contamination with isomers, as hereinbefore described;

vi. the methods of preparing the compounds defined under paragraph (v);

vii. the methods of preparing 5-benzylpyrimidines by using compounds or products of methods, according to any one of paragraphs (i) to (vi), as hereinbefore described;

viii. 5-benzylpyrimides whenever prepared by a method including steps according to any one of paragraphs (ii), (iii), (vi) and (vii).

The present invention, in each of the above aspects, is particularly preferred when the phenyl group is a 3,4-dimethoxy, 3,4,5-trimethoxy or 2-methyl-4,5-dimethoxy group, since there are then produced the especially valuable compounds diaveridine, trimethoprim or ormetoprim, or the respective intermediates therefor.

FLOW SHEET

Reaction Sequence

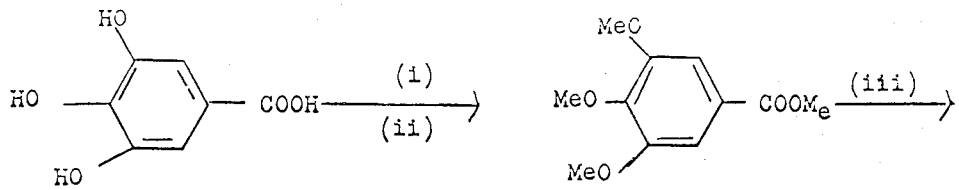

XI

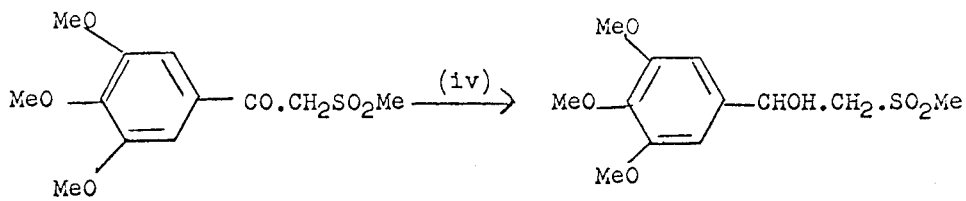

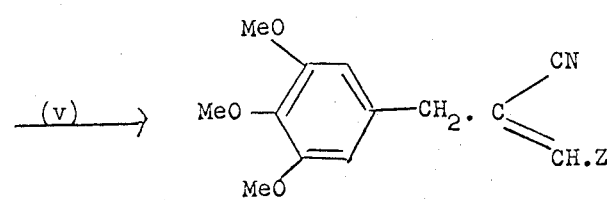

(XII)

THE FOLLOWING EXAMPLES ILLUSTRATE THE INVENTION:-

EXAMPLE 1

3,4,5-Trimethoxybenzaldehyde (98g.), β-anilinopropionitrile (85g.), and dimethylsulfoxide (175 ml.) were heated together to 125° C. A solution of sodium methylate (5g.) in methanol (50ml.) was gradually added and in so doing the reaction temperature rose to 130° C, and this temperature was maintained for a further 17 minutes. The reaction mixture was chilled; water was added to a persistent haze; seeds of β-anilino-αα-3,4,5-trimethoxybenzylacrylonitrile U.V. added; and the mixture was stirred at 25° C until precipitation was copious. Additional water (400ml.) was added, and the product was collected by filtration and reslurried in ice water (600ml.). The collection and reslurry procedures were repeated using cold (~5° C) denatured alcohol (320ml.), and the crystalline β-anilino-α-3,4,5-trimethoxybenzylacrylonitrile was finally collected; washed with cold denatured alcohol (40ml.), and hexane (100ml.). Wt.=115g. (71%; 98% pure by U.V. assay) m.p. 132°–133° C (recrystallised from methanol).

EXAMPLE 2

3,4,5-Trimethoxybenzaldehyde (49 g.), β-anilinopropionitrile (40 g.), and dimethylsulfoxide (85 ml.) were heated together to 130° C, and a solution of potassium hydroxide (2.5 g.) in methanol (12.5 ml.) was added over a 35 min. period. The temperature of the reaction was maintained at 130°–135° C for an additional 30 min., and the reaction mixture was then treated as in Example 1 to give β-anilino-α-3,4,5-trimethoxybenzylacrylonitrile as a crystalline solid. Wt.=57 g. (70%).

EXAMPLE 3

3,4,5-Trimethoxybenzaldehyde (117.5 g; 0.6 mole), β-anilinopropionitrile (101 g.; 0.69 mole), and dry distilled dimethylsulfoxide (348 ml.) were heated together to 40° C until solution was complete. The mixture was chilled to 12° C and a solution of potassium t-butoxide in t-butanol (13.6%; 491 ml.; 0.6 mole) was added over the course of about 10 min. such that the final temperature was about 30° C. The temperature was raised to 40° C and maintained for one hour. t-Butanol was then stripped from the reaction using vacuum to a final pot temperature of 55° C. The residue was chilled to 30° C and water (100 ml.) and denatured ethanol (50 ml.) added. The mixture was seeded and after obvious crystallisation more ice/water (500 ml.) and denatured ethanol (75 ml.) were added. When the final temperature of the mixtue was 5°–10° C the crystalline β-anilino-α-3,4,5-trimethoxybenzylacrylonitrile was collected, and washed with a mixture of cold water/denatured ethanol (85:15; 600 ml.). Wt=181.7 g. (94% pure by U.V. assay; yield 88%.

EXAMPLE 4

3.4-Dimethoxybenzaldehyde (88 g.), β-anilinopropionitrile (82.5 g.), dimethylsulfoxide (160 ml.), and sodium methylate were heated together at 95° C for 2½ hr. The reaction mixture was then chilled to 25° C and diluted with isopropyl alcohol (40 ml.) and water. When crystallisation was obvious further water (200 ml.) was added. The mixture was cooled to 5° C and crystalline β-anilino-α-3,4-dimethoxybenzylacrylonitrile was collected and washed with cold water/isopropylalcohol (1:1). Wt.=99 g. (61%) m.p. 153°–154° C (recrystallised from denatured alcohol).

EXAMPLE 5

Piperonaldehyde (45 g.), β-anilinopropionitrile (52 g.) and dimethylsulfoxide (96 ml.) were heated together to 120° C and a solution of sodium methylate (2.5 g.) in methanol (12 ml.) was added over a 5 min. period. The temperature was maintained at 115°–120° C for 1 hr. and the mixture was then poured into ice-water. The resulting gum was collected by decantation and was likewise washed with water (2 × 100 ml.). Methanol (100 ml.) was then added and the mixture was heated until solution was complete. Cooling to 5° C gave β-anilino-α-piperonylacrylonitrile as a crystalline solid which was collected, and washed with cold methanol, ether, and pentane. Wt.=45 g. (54%) m.p. 150.5°–151° C (recrystallised from methanol).

EXAMPLE 5a

The procedure of Example 3 was repeated using 3,4-dimethoxy-5-bromobenzaldehyde (78 g.) and gave β-anilino-α-3,4-dimethoxy-5-bromobenzylacrylonitrile. Wt.=62 g. (52%) m.p. 151°–154° C.

EXAMPLE 6

Sodium methylate (5.4 g.) in t-butanol (50 ml.) was slowly treated with a solution of 3,4,5-trimethoxybenzaldehyde (20 g.) and β-(p-methylanilino)-propionitrile (17.5 g.) in dimethylsulfoxide (50 ml.). The mixture was stirred at 45° C for one hour and the alcohol then removed in vacuo (bath temperature not greater than 50° C). The mixture was poured into ice-water and the crude product collected and recrystallised from methanol to give β-(p-methylanilino)-α-3,4,5-trimethoxybenzylacrylonitrile. Wt.=30 g. (89%) m.p. 150°–151° C (recrystallised from methanol).

EXAMPLE 7

The procedure of Example 6 was repeated using β-(p-chloroanilino) propionitrile (20 g.) in place of β-(p-methylanilino) propionitrile. Wt. of recrystallised β-(p-chloroanilino)-α-3,4,5-trimethoxybenzylacrylonitrile = 24 g. (67%) m.p. 172°–173° C (recrystallised from methanol).

EXAMPLE 8

The procedure of Example 6 was repeated using β-(p-methoxyanilino) propionitrile (19.5 g.) in place of β-(p-methylanilino) propionitrile. Wt. of recrystallised β-(p-methoxyanilino)-α-3,4,5-trimethoxybenzylacrylonitrile = 11 g. (33%) m.p. 125°–125° C (recrystallised from methanol).

EXAMPLE 9

2-Methyl-4,5-dimethoxybenzaldehyde (18 g.), dimethylsulphoxide (35 ml.), sodium methoxide (1.0 g.), and β-anilinopropionitrile were heated together at 95° C for 1½ hr. The mixture was then poured into ice-water (150 g.), and the resulting solid collected by decantation. The crude product was recrystallised from methanol (100 ml.) and the resulting β-anilino-α-(2-methyl-4,5-dimethoxybenzyl) acrylonitrile was collected, and washed with methanol and hexane. Wt. = 19 g. (60%) m.p. 117°–119° C (recrystallised from ethanol/methanol).

EXAMPLE 10 p-Benzyloxybenzaldehyde (25g.), β-anilinopropionitrile (22 g.), and dimethylsulphoxide (25 ml.) were heated together to 95° C, and a slurry of sodium methoxide (1 g.) in dimethylsulphoxide (20 ml.) was carefully added such that the temperature rose to 105° C. The mixture was heated to 125°–130° and held at that temperature for 1½ hr. The reaction mixture was poured into ice-water (500 ml.), and the resulting solid was collected and washed by decantation. The crude product was slurried in cold ethanol to give β-anilino-α-(p-benzyloxybenzyl) acrylonitrile. Wt.= 27g.

EXAMPLE 11

β-Morpholinopropionitrile (47 g.), sodium methoxide (2 g.), and dimethylsulphoxide (40 ml.) were heated together to 65° C, and a solution of 3,4,5-trimethoxybenzaldehyde (50 g.) in dimethylsulphoxide (40 ml.) was added slowly such that the temperature rose to 70°–75° C. After 3 min. at this temperature the mixture was cooled to 30 ° C, and isopropyl alcohol (30 ml.) and water sufficient to create a persistent haze were added. The mixture was seeded and, after crystallisation was obvious, water (80 ml.) was added. Crystalline β-morpholino-α-3,4,5-trimethoxybenzylacrylonitrile was collected and washed with isopropyl alcohol (50 ml.). Wt. = 73.5 g. (89%) m.p. 115°–117° C (recrystallised from methanol).

EXAMPLE 12

3,4,5-Trimethoxybenzaldehyde (20 g.), β-N-methylanilinopropionitrile (18 g.), dimethylsulphoxide (40 ml.), and sodium methoxide (1 g.) were heated together at 110°–115° C for 1.5 hr. The mixture was poured into ice-water (800 ml.) and the crude product which precipitated gave crystalline β-N-methylanilino-α-3,4,5-trimethoxybenzylacrylonitrile after a slurry in methanol (50 ml.). Wt. = 17 g. (50%) m.p. 121°–122° C (recrystallised from methanol).

EXAMPLE 13

3,4,5-Trimethoxybenzaldehyde (50 g.), β-piperidinopropionitrile (40 g.), dimethylsulphoxide (60 ml.), and sodium methoxide (2 g.) were reacted together at 75° C for 20 min. and on work-up gave β-piperidino-α-3,4,5-trimethoxybenzylacrylonitrile. Wt.=40 g. (50%) m.p. 92°–93° C (recrystallized from methanol).

EXAMPLE 14

3,4,5-Trimethoxybenzaldehyde (25 g.), β-pyrrolidinopropionitrile (20 g.), dimethylsulphoxide (25 ml.) and sodium methoxide (1 g.) were reacted together at 75° C for 10 min., and on work-up gave β-pyrrolidino-α-3,4,5-trimethoxybenzylacrylonitrile. Wt.=28 g. (75%) m.p. 123°–124° C (recrystallised from methanol).

EXAMPLE 15

3,4,5-Trimethoxybenzaldehyde (25 g.), β-N-dimethylaminopropionitrile (16 g.), dimethylsulphoxide (45 ml.), and sodium methoxide (1 g.) were reacted together at 70° C for 10 min., and on work-up gave β-dimethylamino-α-3,4,5-trimethoxybenzylacrylonitrile. Wt.=25 g. (73%) m.p. 122°–123° C (recrystallised from methanol).

EXAMPLE 16

3,4,5-Trimethoxybenzaldehyde (50 g.), β-benzylaminopropionitrile (45 g.), dimethylsulphoxide (80 ml.), and sodium methoxide (2 g.) were heated together at 100° C for 2 hr. and on work-up gave β-benzylamino-α-3,4,5-trimethoxybenzylacrylonitrile. Wt.=32 g. (37%) m.p. 130.5°–131° C (recrystallised from methanol).

EXAMPLE 17

3,4,5-Trimethoxybenzaldehyde (25 g.), β-morpholinopropionitrile (20 g.), sodium methoxide (2 g.), and N,N-dimethylacetamide (25 ml.) were reacted together at 90°–95° C for 1½ hr., and on work-up gave β-morpholino-α-3,4,5-trimethoxybenzylacrylonitrile. Wt.=15 g. (37%).

EXAMPLE 18

β-Morpholinopropionitrile (40 g.), dimethylsulphoxide (40 ml.), and sodium methoxide (2 g.) were heated together at 70° C and a solution of 3,4-dimethoxybenzaldehyde (44 g.) in dimethylsulphoxide (40 ml.) was added. The reaction was held at 75–80° C for 15 min., and then worked-up as in Example 11 to give crystalline β-morpholino-α-3,4-dimethoxybenzylacrylonitrile. Wt.=41 g. (57%) m.p. 130°–131° C (recrystallised from methanol).

EXAMPLE 19

The procedure of Example 18 was repeated using β-dimethylaminopropionitrile (28 g.) in place of β-morpholinopropionitrile, and on work-up gave β-dimethylamino-α-3,4-dimethoxybenzylacrylonitrile. Wt.=31 g. (50%) m.p. 85°–86° C (recrystallised from methanol).

EXAMPLE 20

β-Morpholinopropionitrile (20 g.), dimethylsulphoxide (30 ml.), and sodium methoxide (1 g.) were heated together at 80° C and a solution of piperonaldehyde (19 g.) in dimethylsulphoxide was added. The mixture was reacted at 80° C for 15 min., and on work-up gave β-morpholino-α-piperonylacrylonitrile, Wt.=21 g. (61%) m.p. 85°–85.5° C (recrystallised from methanol).

EXAMPLE 21

The procedure of Example 20 was repeated using 3,4-dimethoxy-5-bromobenzaldehyde (31 g.) in place of piperonaldehyde and on work-up gave β-morpholino-α-3,4-dimethoxy-5-bromobenzylacrylonitrile. Wt.=28 g. (60%) m.p. 94.5°–95° C (recrystallised from denatured ethanol).

EXAMPLE 22

β-Hydroxy-α-3,4,5-trimethoxybenzylacrylonitrile (132 g.), obtained as hereinafter described in Example 62, was refluxed for 10 min. in benzene containing aniline (50 g.). The solvent was removed by evaporation in vacuo to provide crystalline β-anilino-α-3,4,5-trimethoxybenzylacrylonitrile (165 g.; virtually theoretical yield).

EXAMPLE 23

A solution of morpholine (10 ml.) and β-hydroxy-α-3,4,5-trimethoxybenzylacrylonitrile (24.9 g.) in ethanol (100 ml.) was refluxed for 30 min. When cooled the reaction gave β-morpholino-α-3,4,5-trimethoxybenzylacrylonitrile. Wt.=27 g. (85%) m.p. 116°–117° C.

EXAMPLE 24

β-Hydroxy-β-3,4,5-trimethoxyphenethylmethylsulphone (29 g.), β-anilinopropionitrile (16.5 g.) and dimethylsulphoxide (40 ml.) were heated together to 40° C, and a solution of potassium-t-butoxide in t-butanol (13.6%; 83 ml.) was carefully added. The temperature was maintained at 45° C for 1 hr. Alcohol was then removed from the reaction mixture by vacuum evaporation and the residue was poured into ice-water (200 ml.). The crude crystalline product was collected and recrystallised from ethanol to give β-anilino-α-3,4,5-trimethoxybenzylacrylonitrile. Wt.=26 g. (after washing with ethanol and hexane; 80%).

EXAMPLE 25

The procedure of Example 24 was repeated using hexamethylphosphoramide (40 ml.) in place of dimethylsulphoxide, and on work-up β-anilino-α-3,4,5-trimethoxybenzylacrylonitrile was obtained. Wt.=26 g. (80%) m.p. 126°–128° C.

EXAMPLE 26

β-Hydroxy-β-3,4,5-trimethoxyphenethylmethylsulphone (5 g.), β-anilinopropionitrile (3 g.) dimethylsulphoxide (20 ml.), and a solution of potassium hydroxide in methanol (20%; 2 ml.) were reacted together at 90°–95° C for 20 min. Work-up gave β-anilino-α-3,4,5-trimethoxybenzylacrylonitrile (3 g.; 53%). m.p. 126°–129° C (recrystallised from ethanol).

EXAMPLE 27

The procedure of Example 26 was repeated using hexamethylphosphoramide (20 ml. in place of dimethylsulphoxide and on work-up gave β-anilino-α-3,4,5-trimethoxybenzylacrylonitrile (2 g.; 36%) m.p. 125°–127° C (recrystallised from ethanol).

EXAMPLE 28

The procedure of Example 26 was repeated using sodium methoxide (0.5 g.) in place of potassium hydroxide in methanol, and on work-up gave β-anilino-α-3,4,5-trimethoxybenzylacrylonitrile. Wt.=3 g. (54%) m.p. 128°–130° C.

EXAMPLE 29

β-Hydroxy-β-3,4,5-trimethoxyphenethylmethylsulphone (10 g.), β-anilinopropionitrile (5.1 g.), hexamethylphosphoramide (20 ml.), and sodium methoxide (1 g.) were reacted together at 60° C for 30 min., and on work-up gave β-anilino-α-3,4,5-trimethoxybenzylacrylonitrile. Wt.=6 g. (54%) m.p. 127°–129° C.

EXAMPLE 30

The procedure of Example 28 was repeated using N,N-dimethylacetamide (25 ml.) in place of dimethylsulphoxide, and on work-up gave β-anilino-α-3,4,5-trimethoxybenzylacrylonitrile. Wt.=2.5 g. (45%) m.p. 125°–128° C.

EXAMPLE 31

β-Hydroxy-β-3,4,5-trimethoxyphenethylmethylsulphoxide (5.4 g.), β-anilinopropionitrile (3 g.), dimethylsulphoxide (25 ml.), and sodium methylate (0.5 g.) were reacted together at 90°–95° C for 1 hr. The mixture was then poured into ice-water; the solid collected; and recrystallised from denatured ethanol to give β-anilino-α-3,4,5-trimethoxybenzylacrylonitrile. Wt.=2 g. (30%) m.p. 125°–127° C.

EXAMPLE 32

The procedure in Example 31 was repeated using potassium hydroxide (2 g.) in methanol (5 ml.) in place of sodium methoxide, and on work-up gave β-anilino-α-3,4,5-trimethoxybenzylacrylonitrile. Wt.=2 g. (30%) m.p. 125°–128° C.

EXAMPLE 33

The procedure in Example 31 was repeated using hexamethylphosphoramide in place of dimethylsulphoxide and sodium methylate (2 g.), and on work-up gave β-anilino-α-3,4,5-trimethoxybenzylacrylonitrile. Wt.=2 g. (30%) m.p. 125°–129° C.

EXAMPLE 34

The procedure in Example 31 was repeated using potassium-t-butoxide in t-butanol (13.6%; 15 ml.) in place of sodium methoxide, and on work-up gave β-anilino-α-3,4,5-trimethoxybenzylacrylonitrile. Wt.=1 g. (15%) m.p. 128°–130° C.

EXAMPLE 35

The procedure in Example 34 was repeated using hexamethylphosphoramide (25 ml.) in place of dimethylsulphoxide, and on work-up gave β-anilino-α-3,4,5-trimethoxybenzylacrylonitrile. Wt.=1 g. (15%) m.p. 123°–126° C.

EXAMPLE 36

β-Morpholinopropionitrile (3.0 g.), β-hydroxy-β-3,4,5-trimethoxyphenethylmethylsulphone (2.9 g.), sodium methoxide (0.3 g.) and hexamethylphosphoramide (6 ml.) were reacted together at 60°–65° C for 40 min., and then poured into ice-water (50 ml.). The crude solid was collected by decantation and recrystalised from ethanol (10 ml.) to give β-morpholino-α-3,4,5-trimethoxybenzylacrylonitrile. Wt.=2 g. (~60%).

EXAMPLE 37

The procedure in Example 36 was repeated using benzyltrimethylammonium hydroxide in place of sodium methoxide and on work-up β-morpholino-α-3,4,5-trimethoxybenzylacrylonitrile was obtained in 50% yield.

EXAMPLE 38

3,4,5-Trimethoxybenzaldehyde (40 g.), β-anilinopropionitrile (44 g.), sodium methoxide (32 g.), and methanol were heated together under reflux for 45 min. The reaction mixture was then poured into ice-water (200 ml.) and the resulting thick oil was collected and washed by decantation. Recrystallisation from ethanol gave crystalline β-anilino-α-3,4,5-trimethoxybenzylacrylonitrile. Wt.=42 g. (after washing with ethanol and pentane; 64%).

EXAMPLE 39

3,4-Dimethoxybenzaldehyde (41.5 g.), β-anilinopropionitrile (38.5 g.), sodium methoxide (40 g.) and methanol (200 ml.) were reacted under reflux for 3 hr. The solvent was then removed by evaporation in vacuo and the resulting paste was recrystallised from methanol to give β-anilino-α-3,4,-dimethoxybenzylacrylonitrile. Wt.=55 g. (75%) m.p. 153°–154° C (recrystallised from ethanol).

EXAMPLE 40

β-Morpholino-α-3,4,5-trimethoxybenzylacrylonitrile (318 g.), aniline (107 g.) and glacial acetic acid (69 g.) were heated together at 95° C for 45 min. Isopropanol (300 ml.) was then added and the mixture was cooled to 30° C; seeded; and treated with water (300 ml.) after crystallisation was obvious. Filtration gave β-anilino-α-3,4,5-trimethoxybenzylacrylonitrile. Wt.=296 g. (after washing with water and isopropanol; 91%).

EXAMPLE 41

Aniline hydrochloride, from aniline (10 g.) and conc. hydrochloric acid (12 ml.), and β-morpholino-α-3,4,5-trimethoxybenzylacrylonitrile (30 g.) were reacted together in refluxing isopropanol (50 ml.) for 15 min. Water (25 ml.) was added and on cooling crystals of β-anilino-α-3,4,5-trimethoxybenzylacrylonitrile were obtained. Wt.=29 g.

EXAMPLE 42

β-Methoxy-α-3,4,5-trimethoxybenzylidenepropionitrile (53 g.), obtained according to method described in British Pat. No. 957,797, morpholine (100 ml.), sodium methoxide (14 g.), and methanol (53 ml.) were heated together at 90° C for 15 min. The solvent was removed by evaporation in vacuo and the residue was poured into ice-water. The thick oil which separated was collected and washed by decantation and on treatment with ether gave crystalline β-morpholino-α-3,4,5-trimethoxybenzylacrylonitrile. Wt.=53 g. (88%).

EXAMPLE 43

3,4,5-Trimethoxybenzaldehyde (25 g.), β-morpholinopropionitrile (20 g.), methanol (50 ml.), and sodium methoxide (1 g.) were heated together under reflux for 72 hr. Solvent was then removed in vacuo and the residue was crystallised from diethylether (100 ml.) to give β-morpholino-α-3,4,5-trimethoxybenzylidenepropionitrile. Wt.=18 g. (44%) m.p. 100.5°–102° C (recrystallised from methanol).

EXAMPLE 44

3,4-Dimethoxybenzaldehyde (21 g.), β-morpholinopropionitrile (22 g.), sodium methylate (1 g.) and methanol (50 ml.) were heated together under reflux for 20 hr. Work-up as in Example 43 gave β-morpholino-α-3,4-dimethoxybenzylidenepropionitrile. Wt.=25 g. (67%) m.p. 95°–97° C. (recrystallised from methanol).

EXAMPLE 45

The procedure of Example 43 using β-piperidinopropionitrile (20 g.) gave β-piperidino-α-3,4,5-trimethoxybenzylidenepropionitrile. Wt.=32 g. (79%) m.p. 60°–62° C (recrystallised from isopropanol).

EXAMPLE 46

The procedure of Example 43 using β-pyrrolidinopropionitrile (20 g.) gave β-pyrrolidino-α-3,4,5-trimethoxybenzylidenepropionitrile as an oil. Wt.=37 g. (96%).

EXAMPLE 47

The procedure of Example 43 using β-dimethylaminopropionitrile (18 g.) gave β-dimethylamino-α-3,4,5-trimethoxybenzylidenepropionitrile. Wt.=20 g. (57%) m.p. 81°–83° C (recrystallised from methanol).

EXAMPLE 48

Piperonaldehyde (30 g.), β-morpholinopropionitrile (40 g.), methanol (75 ml.) and sodium methylate (1.5 g.) were heated together under reflux for 20 hr. Solvent was removed in vacuo and the residue recrystallised from ether, after treatment with aqueous sodium bisulphite, to give β-morpholino-α-piperonylidenepropionitrile. Wt.=29 g. (53%) m.p. 80°–85° C (recrystallised from methanol).

EXAMPLE 49

β-Morpholino-α-3,4,5-trimethoxybenzylidenepropionitrile (3 g.), dimethylsulphoxide (10 ml.) and sodium methoxide (0.1 g.) were heated together at 50°–60° C for 10 min. Work-up gave crystalline β-morpholino-α-3,4,5-trimethoxybenzylacrylonitrile. m.p. 115°–117° C.

EXAMPLE 50

The procedure of Example 49 was repeated using β-dimethylamino-α-3,4,5-trimethoxybenzylidenepropionitrile (4 g.) and on work-up gave β-dimethylamino-α-3,4,5-trimethoxybenzylacrylonitrile. Wt.=3.2 g. (80%) m.p. 119°–122° C (recrystallized from methanol).

EXAMPLE 51

The procedure of Example 49 was repeated using β-piperidino-α-3,4,5-trimethoxybenzylidenepropionitrile (3.5 g.) and in work-up gave β-piperidino-α-3,4,5-trimethoxybenzylacrylonitrile. Wt.=2.7 g. (77%) m.p. 89°–92° C.

EXAMPLE 52

β-Dimethylamino-α-3,4,5-trimethoxybenzylidenepropionitrile (2 g.), hexamethylphosphoramide (10 ml.), and sodium methoxide (0.05 g.) were heated together at 30°C. Conversion to β-dimethylamino-α-3,4,5-trimethoxybenzylacrylonitrile was complete in 1 min. and this compound was obtained on work-up. Wt.=1 g. (50%) m.p. 118°–120° C (recrystallised from methanol).

EXAMPLE 53

β-Dimethylamino-α-3,4,5-trimethoxybenzylidenepropionitrile (2 g.), dimethylsulphoxide (10 ml.) and potassium-t-butoxide (0.05 g.) at 30° for 1 min. gave β-dimethylamino-α-3,4,5-trimethoxybenzylacrylonitrile. Wt.=1 g. (50%) m.p. 119°–121° C.

EXAMPLE 54

β-Dimethylamino-α-3,4,5-trimethoxybenzylidenepropionitrile (4 g.), hexamethylphosphoramide (10 ml.), and potassium-t-butoxide (0.05 g.) at 30° C for 1-2 min. gave β-dimethylamino-α-3,4,5-trimethoxybenzylacrylonitrile. Wt.=3 g. (75%) m.p. 117°–119° C.

EXAMPLE 55

β-Dimethylamino-α-3,4,5-trimethoxybenzylidenepropionitrile (2 g.), dimethylsulphoxide (10 ml.), and 3 drops of a saturated solution of potassium hydroxide in methanol at 40° C for 5 min. gave β-dimethylamino-α-3,4,5-trimethoxybenzylacrylonitrile. Wt.=1.3 g. (65%) m.p. 118°–120° C.

EXAMPLE 56

The procedure as in Example 55 using hexamethylphosphoramide in place of dimethylsulphoxide in 2 min. gave β-dimethylamino-α-3,4,5-trimethoxybenzylacrylonitrile. Wt.=1.8 g. (90%) m.p. 121°–123° C.

EXAMPLE 57

The procedure as in Example 49 using β-pyrrolidino-α-3,4,5-trimethoxybenzylidenepropionitrile gave β-pyrrolidino-α-3,4,5-trimethoxybenzylacrylonitrile. m.p. 123°–124° C.

EXAMPLE 58

The procedure as in Example 52 using β-morpholino-α-3,4,-dimethoxybenzylidenepropionitrile gave β-morpholino-α-3,4-dimethoxyacrylonitrile. m.p. 127°–129° C.

EXAMPLE 59

The procedure as in Example 49 using β-morpholino-α-piperonylidenepropionitrile (5.0 g.) gave β-morpholino-α-piperonylacrylonitrile. Wt.=4.5 g. (90%) m.p. 82°–84° C.

EXAMPLE 60

The procedure as in Example 50 using N,N-dimethylacetamide in place of dimethylsulphoxide gave β-dimethylamino-α-3,4,5-trimethoxybenzylacrylonitrile in 83% yield. m.p. 121°–123° C.

EXAMPLE 61

The procedure as in Example 52 using benzyltrimethylammonium hydroxide in place of sodium methoxide gave β-dimethylamino-α-3,4,5-trimethoxybenzylacrylonitrile in 86% yield. m.p. 122°–123° C.

EXAMPLE 62

β-Morpholino-α-3,4,5-trimethoxybenzylacrylonitrile (157 g.) was treated with conc. hydrochloric acid (75 ml.) in water (180 ml.) at 60° C for 15 min. The reaction mixture was cooled, extracted with chloroform (100 ml.; 75 ml.; 75 ml.), and the extracts were backwashed with water (75 ml.). Removal of solvent gave β-hydroxy-α-3,4,5-trimethoxybenzylacrylonitrile as a thick oiil. Wt.=125 g. (theory).

EXAMPLE 63

β-Hydroxy-α-3,4,5-trimethoxybenzylacrylonitrile (70 g.) in methanol (150 ml.) at 10° C was treated with dimethylsulphate (39 g.). To the mixture was then gradually added a solution of potassium hydroxide (20 g.) in methanol (30 ml.) and water (12 ml.) and the reaction was then kept at 10° C for 15 min. The mixture was next heated to 60° C for 15 min.; then cooled; and finally solvent was removed to a residue which was slurried in water (100 ml.) and extracted into chloroform (2 × 80 ml.). The chloroform extract, after backwashing with water (70 ml.), drying, and treatment with charcoal, was evaporated to dryness to give β-methoxy-α-3,4,5-trimethoxybenzylacrylonitrile. Wt.=61 g. (80%).

EXAMPLE 64

β-Anilino-α-3,4,5-trimethoxybenzylacrylonitrile (32 g.) and a solution of guanidine hydrochloride (19 g.) and sodium methoxide (13 g.) in denatured ethanol (100 ml.) were heated under reflux for 2½ hr. Solvent (31 ml.) was boiled off and the mixture was cooled to 5° C. The resulting crystals of 2,4-diamino-5-(3',4',5'-trimethoxybenzyl)pyrimidine were collected and washed with denatured ethanol and acetone. Wt.=27 g. (94%) m.p. 198°–200° C.

Using methanol in place of denatured alcohol gave 2,4-diamino-5-(3',4',5'-trimethoxybenzyl)pyrimidine in 86% yield after 6 hr. reflux; with isopropanol the reaction was over in 2 hrs. and the yield was 78%.

EXAMPLE 65

The product from Example 6 was converted to 2,4-diamino-5-(3',4',5'-trimethoxybenzyl)pyrimidine by the procedure of Example 64 in 2 hr. Yield=90%.

EXAMPLE 66

The product from Example 7 was converted to 2,4-diamino-5-(3',4',5'-trimethoxybenzyl)pyrimidine by the procedure of Example 64 in 2 hr. Yield=90%.

EXAMPLE 67

The product from Example 8 was converted to 2,4-diamino-5-(3',4',5'-trimethoxybenzyl)pyrimidine by the procedure of Example 64 in 4½ hr. Yield=90%.

EXAMPLE 68

The procedure of Example 64 was repeated using β-anilino-α-3,4-dimethoxybenzylacrylonitrile (29.4 g.) and gave 2,4-diamino-5-(3',4'-dimethoxybenzyl)pyrimidine. Wt.=25.5 g. (98%) m.p. 230°–233° C.

EXAMPLE 69

The procedure of Example 64 was repeated using β-anilino-α-piperonylacrylonitrile (28 g.) and gave 2,4-diamino-5-piperonylpyrimidine. Wt.=22 g. (89.5%) m.p. 252°–253° C (recrystallised from denatured alcohol).

EXAMPLE 70

The procedure of Example 64 was repeated using β-anilino-α-2-methyl-4,5-dimethoxybenzylacrylonitrile (16 g.) and after 18–20 hr. reflux gave 2,4-diamino-5-(2'-methyl-4',5'-dimethoxybenzyl)pyrimidine. Wt.=11.5 g. (92%) m.p. 230°–231° C.

*EXAMPLE 71

The procedure of Example 64 was repeated using β-anilino-α-3,4-dimethoxy-5-bromobenzylacrylonitrile (62 g.) and gave 2,4-diamino-5-(3',4'-dimethoxy-5'-bromobenzyl)pyrimidine. Wt.=38 g. (70%) m.p. 203.5°–205° C.

EXAMPLE 72

The procedure of Example 64 was repeated using β-anilino-α-p-benzyloxybenzylacrylonitrile (25 g.) and gave after 4 hr. reflux 2,4-diamino-5-(p-benzyloxybenzyl)pyrimidine. Wt.=20.5 g. This was converted to its acetate salt by treatment with acetic acid. Wt.=15 g.

EXAMPLE 73

2,4-Diamino-5-(p-benzyloxybenzyl)pyrimidine acetate (4.6 g.) in methanol (200 ml.) was hydrogenated at low pressure over 5% Palladium/Carbon. The filtrate after removal of catalyst was evaporated and the resulting residue purified by dissolution in hot dilute acetic acid and re-precipitatin with ammonium hydroxide to pH 9. Crystalline 2,4-diamino-5-(p-hydroxybenzyl)-pyrimidine was collected and washed with water. Wt.=2.16 g. m.p. 300°–303° C.

EXAMPLE 74

β-Morpholino-α-3,4,5-trimethoxybenzylacrylonitrile (32 g.) guanidine carbonate (34 g.) and dimethylsulphoxide (50 ml.) were heated together at 160° C for 1 hr. with good stirring. The reaction mixture was cooled and poured into ice-water (200 ml.), and gave 2,4-diamino-5-(3′,4′,5′-trimethoxybenzyl)pyrimidine which was collected and washed with water and acetone. Wt.=23.6 g. (80%) m.p. 196°–198° C.

EXAMPLE 75

The procedure of Example 74 was repeated using β-N-methylanilino-α-3,4,5-trimethoxybenzylacrylonitrile and gave 2,4-diamino-5-(3′,4′,5′-trimethoxybenzyl)pyrimidine.

EXAMPLE 76

The procedure of Example 74 was repeated using β-piperidino-α-3,4,5-trimethoxybenzylacrylonitrile and gave 2,4-diamino-5-(3′,4′,5′-trimethoxybenzyl)-pyrimidine.

EXAMPLE 77

The procedure of Example 74 was repeated using β-pyrrolidino-α-3,4,5-trimethoxybenzylacrylonitrile and gave 2,4-diamino-5-(3′,4′,5′-trimethoxybenzyl)-pyrimidine.

EXAMPLE 78

The procedure of Example 74 was repeated using β-dimethylamino-α-3,4,5-trimethoxybenzylacrylonitrile and gave 2,4-diamino-5-(3′,4′,5′-trimethoxybenzyl)pyrimidine.

EXAMPLE 79

The procedure of Example 74 was repeated using β-benzylamino-α-3,4,5-trimethoxybenzylacrylonitrile and gave 2,4-diamino-5-(3′,4′,5′-trimethoxybenzyl)-pyrimidine.

EXAMPLE 80

The procedure of Example 74 was repeated using β-morpholino-α-3,4-dimethoxybenzylacrylonitrile and gave 2,4-diamino-5-(3′,4′-dimethoxybenzyl)pyrimidine.

EXAMPLE 81

The procedure of Example 74 was repeated using β-dimethylamino-α-3,4-dimethoxybenzylacrylonitrile and gave 2,4-diamino-5-(3′,4′-dimethoxybenzyl)-pyrimidine.

EXAMPLE 82

The procedure of Example 74 was repeated using β-morpholino-α-piperonylacrylonitrile and gave 2,4-diamino-5-piperoylpyrimidine.

EXAMPLE 83

The procedure of Example 74 was repeated using β-morpholino-α-3,4-dimethoxy-5-bromobenzylacrylonitrile and gave 2,4-diamino-5-(3′,4′-dimethoxy-5′-bromobenzyl)pyrimidine.

EXAMPLE 84

The procedure of Example 64 was repeated using β-methoxy-α-3,4,5-trimethoxybenzylacrylonitrile (54 g.) and after 20 hr. reflux gave 2,4-diamino-5-(3′,4′,5′-trimethoxybenzyl)pyrimidine. Wt.=56 g. (94%) m.p. 198°–200° C.

EXAMPLE 85

Under the conditions of Example 24 the β-hydroxy-β-(3,4-dichlorophenethylmethylsulfone, β-hydroxy-β(o, meta, p-iodophenyl)methylsulfones and β-hydroxy-β-(α-bromophenethylsulfones) were condensed with β-anilinopropionitrile to yield the corresponding β-anilino-α-halogenobenzylacrylonitriles.

EXAMPLE 86

The procedure of Example 64 was repeated using the products of Example 85 to give 2,4 -Diamino-5(3′, 4′-dichlorobenzyl) pyrimidine, m.p. 237°–239°, 2,4-Diamino-5-(o-iodobenzyl) pyrimidine, m.p. 265°–267°, 2,4-Diamino-5-(m-iodobenzyl) pyrimidine, m.p. 220.5°–222°, 2,4-Diamino-5-(p-iodobenzyl) pyrimidine, m.p. 246°–248°, and 2,4-diamino-5-(o-bromobenzyl) pyrimidine, m.p. 248°–250°.

EXAMPLE 87

β-hydroxy-α-3,4,5-trimethoxy-benzylacrylonitrile 25 grams, denatured ethanol (70 ml.) 2,4-dimethyl aniline (14 ml.) refluxed together for 1 hr. Solvent removed by evaporation and vacuum and the residue was poured into ice water. The resulting thick gum was collected and recrystallized from methanol to give crystalline β-2,4-dimethylanidino -α-3,4,5-trimethoxybenzylacrylonitrile. Wt.=11g. (31% yield) M.P. 123°–125° C.

EXAMPLE 88

Procedure of Example 87 was repeated using 3,4,5-trimethoxyaniline and gave β-3,4,5-trimethoxybenzylacrylonitrile in 65% yield. M.P. 156°–161° C. Recrystallized from denatured ethanol.

EXAMPLE 89

Procedure of Example 87 was repeated using 2,5-dichloroaniline and gave β-2,5,-dichloroanilino -α-3,4,5-trimethoxybenzylacrylonitrile. 20 g, 51% yield. A sample recrystallized from denatured ethanol melted at 130° C, resolidified, and then remelted at 150° C.

EXAMPLE 90

Procedure of Example 87 was repeated using α-napthylamine 14.3gr. and gave crystalline β-1-napthylamino-α-3,4,5-trimethoxybenzylacrylonitrile. Wt.=26 gr. 70% yield, melting pt. 107° – 109° C.

EXAMPLE 91

The product from Example 87 was converted to trimethoprim by the procedure of Example 64 in 4 hrs. Yield 92%.

EXAMPLE 92

The product from Example 88 was converted to trimethoprim by the procedure of Example 64 in 3 hrs. Yield above 90%.

EXAMPLE 93

The product from Example 89 was converted to trimethoprim by the procedure of Example 64 in 1.5 hrs. Yield 95%. This reaction was repeated as in Example 64 except at room temperature and useful yield of trimethoprim was obtained in several hrs.

EXAMPLE 94

The product from Example 90 was converted to trimethoprim by the procedure of Example 64 in several hrs. Yield 72%.

EXAMPLE 95

Methyl α-(3,4,5-trimethoxyacetophenone) Sulphone

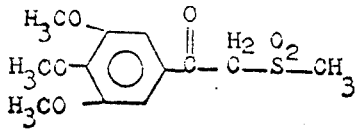

Change into a 500 ml. three necked flask equipped with stirrer and reflux condenser, 27 gms. (0.69M) sodium amide, 225 ml. dimethylsulphoxide and 56.5 gm. dimethylsulphone (0.6M). Heat to 55° C for one hour with stirring, and cool to 50° C. Add 65.4 gm. (0.29M) 3,4,5-trimethoxymethylbenzoate and heat to 60° C for one hour to complete the reaction.

Pour the mixture onto 1100 gm. of ice and acidify with 180 ml. dilute HCl (1:1). Cool in an ice bath and filter the crystalline product. Wash with 2×150ml. of ice water and 2×100 ml. ice cold lower alcohol such as ethanol. Air dry overnight or vacuum dry at 40° C to constant weight. The yield will be 74 gm. or 88% of theory of suitable intermediate for the next step. A.N. Sample M.P. 147°–148° C Recrystallized from Ethanol

|   | Calculated | Found |
|---|---|---|
| C | 49.98 | 49.8 |
| H | 5.59 | 5.54 |

EXAMPLE 96

Reduction of methyl α(3,4,5-trimethoxyacetophenone) sulphone to the corresponding alcohol

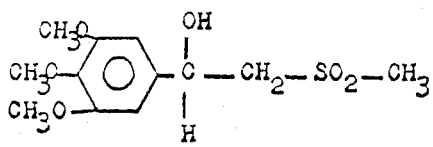

Set up a 3 neck 1 liter flask equipped with a stirrer in an ice bath. Charge with 38.1 gm. of methyl α(3,4,5-trimethoxyacetophenone) sulphone, 100 ml. desalted water and 30 ml. ethanol and cool this slurry to +15° C. Add portion wise a precooled solution of 2 gm. sodium borohydride in 40 ml. desalted water. The first few ml. will cause a slight foaming but it can be controlled easily with a few ml. of ethanol. Additional ethanol can be used to wash down the sides of the reaction flask.

At the end of the addition of the borohydride remove the cooling bath and stir for one hour. Completion of the reaction is checked by U.V. Cool the slurry to +2° C and filter all solids. Wash with small amounts of ice water and dry in vacuum oven at 50° C to constant weight. The yield will be 34.2 gm. or 89.3% of theory. A.N. Sample M.P. 153°–154° C Recrystallized from ethanol

|   | Calculated | Found |
|---|---|---|
| C | 49.7 | 49.39 |
| H | 6.24 | 6.27 |

EXAMPLE 97

ω-(Methylsulfinyl)3,4,5-Trimethoxyacetophenone

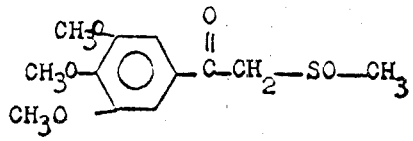

Into a three necked flask, equipped with condenser, stirrer and thermometer, charge 4.0 gm. sodium amide (hexane washed) and 75 ml. dimethyl sulphoxide (distilled and dried). Slowly warm (in an external water bath) to 45° C and the reaction begins. Raise termperature gradually to 60° C and maintain for one (1) hour, to complete.

Cool to +15° and add dropwise a solution of 12 gm. 3,4,5-trimethoxymethylbenzoate in 25 ml. of dimethylsulphoxide. Keep the temperature between 20°–25° C by external cooling. Stir ½ hour at room temperature and quench into 300 ml. ice water. Carefully acidify to pH 5/6 with cold dilute hydrochloric acid.

Extract into chloroform 3×100 ml., wash the organic layer with 4x50 ml. water, dry over sodium sulphate, filter and flash evaporate all solvent.

The heavy oil will weigh 15 gm. and slowly crystallize on standing.

To purify; dissolve the thick oil in 75 ml. ethyl acetate, charcoal and cool the filtrate in an ice acetone bath. Filter and dry the white solid. Wt. = 10 gm. ≈ 70% yield. M.P. 113°–115° C.

A.N. Sample M.P. 115°–116° C Recrystallized from acetone

|   | Calculated | Found |
|---|---|---|
| C | 53.05 | 52.69 |
| H | 5.92 | 5.84 |

EXAMPLE 98

β-Hydroxyβ-3,4,5-trimethoxyphenethylmethylsulphoxide

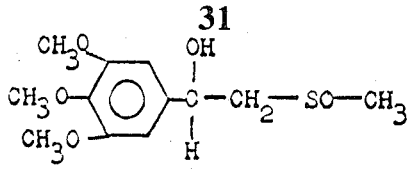

Combine 14 gm.ω(methylsulfinyl)3,4,5-trimethoxyacetophenone, 50 ml. desalted water and 35 ml. methanol. Cool to +15° C and with magnetic stirring add slowly a solution of 0.5 gm. sodium borohydride in 10 ml. water. The reaction is exothermic but can be controlled between 15–20° C with external cooling.

Stir at room temperature for 2 hours, check for completion by U. V. and finally strip off methanol by vacuum at 45°–50° C. Extract the aqueous solution with 3×75 ml. chloroform, wash with the organic layer 1×75 ml. water, dry over magnesium sulphate, filter and evaporate to a clear thick oil. A few drops of ethyl acetate causes complete crystalization. Weight = 14 gm. This is suitable for use in the next step without further purification. A.N. Sample M.P. 150°–155° C (Isomers) Recrystallized from Ethyl Acetate.

|   | Calculated | Found* |
|---|---|---|
| C | 52.4 | 52.37 |
| H | 6.61 | 6.70 |

*Hexamethylphosphoramide has been substituted for the dimethyl sulphoxide as well as potassium hydroxide in methanol for the sodium methylate with the same results in all cases.

EXAMPLE 99

α(3,4,5-Trimethoxybenzyl)β-anilinoacrylonitrile

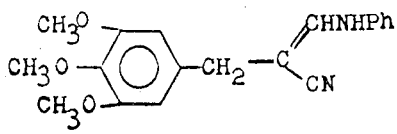

Combine in a flask at room temperature 5.4 gm. β-hydroxy-β-3,4,5-trimethoxyphenethyl methyl sulphoxide, 3 gm. β-anilinopropionitrile, 25 ml. dimethylsulphoxide and 2.0 gm. sodium methylate. Warm slowly with stirring, on a steam bath up to 90°–95° C. It gets very dark in color. Reaction, by U.V., is complete in 20 minutes at 95° C.

Quench in ice water and wash the dark oily precipitate by decantation. Dissolve in 15 ml. of ethanol and cool. Filter the heavy yellow crystalline precipitate, wash with cold ethanol and hexane. Dry. Wt. = 2 gm. ≈ 31% yield. The U.V., I.R., and M.P. are identical to that prepared from the 3,4,5-trimethoxybenzaldehyde and β-anilinopropionitrile. Ph = phenyl.

EXAMPLE 100

α(3,4,5-trimethoxybenzyl)-β-anilinoacrylonitrile

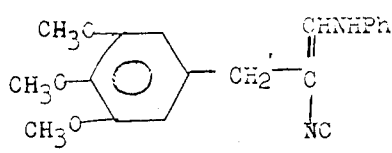

In a three neck flash equipped with stirrer, condenser and thermometer, charge 29 gm. β-hydroxy-β-3,4,5-trimethoxyphenethylmethylsulphone, 16.5 gm. β-anilinopropionitrile and 40 ml. dimethylsulphoxide. Warm to 40° C with stirring, and gradually add 83 ml. of a 13.6% solution of potassium tertiary butoxide in tertiary butanol. Maintain internal temperature at 45° C for one hour and check for completion by U.V.

Strip as much alcohol as possible by vacuum using an external water bath (70° C) and quench in ice water (200 ml.). Stir until the thick oil turns crystalline and filter. Wash the cake with ice water and finally hexane. Vacuum dry at 35° C to constant weight. The yield will be 32 gm.* or theory of crude α-(3,4,5-trimethoxybenzyl-β-anilinoacrylonitrile). The U.V. is satisfactory and it may be used directly in the preparation of Trimethoprim.

*Recrystallisation. Dissolve the crude intermediate in 75 ml. hot ethanol. Cool in ice/acetone bath (preferably overnight) and filter. Wash the cake with cold ethanol (15 ml.) and hexane. Vacuum dry. Weight = 26+gm. ≈80% yield.

EXAMPLE 101

Trimethyl Gallic Acid

A solution of sodium hydroxide (904 g) and water (5642 g) and ice, so that the final temperature was 0° C, was prepared in a 12 liter three-neck round-bottomed flask equipped with stirrer, temperature probe, Y-tube and dip tube. The reaction vessel was purged continuously with a stream of nitrogen bubbled through the solution. Gallic acid (564 g) was added, the heat of solution raising the temperature to ca. 10° C. Dimethyl sulphate (575.9 ml) was added, the temperature allowed to rise to 20°–25° C and then controlled by means of an ice bath for 20 minutes (the temperature rise being very gradual). Two subsequent portions of dimethyl sulphate of equal quantity were added and the temperature maintained for 20 minutes at 30°–35° C and 10 minutes at 40°–45° C respectively. The Y-tube was removed and replaced with a reflux condenser. The mixture was refluxed for 2 hours on mantle, then chilled to 50° C in an ice bath and the pH adjusted to 3–4 with cone hydrochloric acid (ca. 260 ml). Cooling was continued to 10° C and the product collected. The product was washed with ice water (1000 ml) and dried in vacuo at 60° C overnight. The yield was 565 g. of crude trimethyl gallic acid (contaminated with a small quantity of ester) with an m.p. of 139°–154° C (89% yield).

EXAMPLE 102

Trimethyl gallic acid (565 g) and methanol (2300 ml) were mixed, which was then heated to 55° C for 5 hours. While anhydrous hydrogen chloride (46 g) was passed into the mixture. The reaction mixture was poured into an ice and water mixture (8 liters) containing ION sodium hydroxide solution (290 ml) under stirring. The slurry of solids was filtered, washed with ice water and dried in vacuo at 50° C to give 3,4,5-trimethoxymethyl benzoate, wt. = 523g., m.p. of 87°–88° C.

Sodamide (27 g. 0.69 m), dimethylsulphoxide (225 ml.) and dimethylsulphone (56.5 g. 0.6 m) were heated together to 55° C for one hour and cooled to 50° C. 3,4,5-Trimethoxymethylbenzoate (65.4g. 0.29 mole) was added, and the mixture heated to 60° C for one hour to complete the reaction.

The mixture was poured into ice (1100 g), acidified with dilute (1:1) hydrochloric acid (180 ml) and cooled in an ice bath. The crystalline product was filtered, washed with ice water (2 × 150 ml) and ice-cold ethanol (2 × 100 ml). Air drying overnight gave methyl-α-(3,4,5-trimethoxyacetophenone) sulphone, wt. = 74 g., m.p. 147°–148° C.

Methyl-α-(3,4,5-trimethoxyacetophenone) sulphone (38.1 g), desalted water (100 ml) and ethanol (30 ml) were mixed and cooled to 15° C. A pre-cooled solution of sodium borohydride (2 g) in desalted water (40 ml) was gradually added. The cooling bath was then removed and the reaction mixture stirred for one hour. The slurry was cooled to 2° C, the solids filtered washed with iced water, and dried in vacuo at 50° C to give 34.2 g. of the corresponding β-hydroxy-β-3,4,5-trimethoxyphenethylsulphone, m.p. 153°–154° C.

a. The above sulphone (29 g), β-anilinopropionitrile (16.5 g), and dimethylsulphoxide (40 ml.) were heated together to 40° C, and a solution of potassium t-butoxide in t-butanol (13.6%; 83 ml) was carefully added. The temperature was maintained at 45° C for one hour. The alcohol was then removed from the reaction mixture by vacuum evaporation and the residue was poured into ice-water (200 ml.). The crude crystalline product was collected and recrystallised from ethanol to give β-anilino-α-3,4,5-trimethoxybenzylacrylonitrile. Wt. = 26 g. (after washing with ethanol and hexane).

Under the conditions described above under a). the following sulphones were condensed with β-anilinopropionitrile to yield the corresponding β-anilino-α-halogenobenzylacrylonitriles:

b. β-hydroxy-β-(3,4-dichloro-phenethyl)methyl sulphone produced β-anilino-α-3,4-dichlorobenzylacrylonitrile;

c. β-hydroxy-β-(2-iodophenethyl)methyl sulphone produced β-anilino-α-2-iodobenzylacrylonitrile;

d. β-hydroxy-β-(3-iodophenethyl)methyl sulphone produced β-anilino-α-3-iodobenzylacrylonitrile;

e. β-hydroxy-β-(4-iodophenethyl)methyl sulphone produced β-anilino-α-4-iodobenzylacrylonitrile;

f. β-hydroxy-β-(2-bromophenethyl)methyl sulphone produced β-anilino-α-2-bromobenzylacrylonitrile.

EXAMPLE 103

A three-necked flask, equipped with condenser, stirrer and thermometer, was charged with hexane-washed sodium amide (4.0 g) and distilled and dried dimethyl sulphoxide (75 ). The mixture was slowly warmed in an external water bath to 45° C and the reaction began. The temperature was raised gradually to 60° C and maintained for one hour, to complete the reaction.

The mixture was cooled to +15° C and a solution of 3,4,5-trimethoxymethylbenzoate (12 g) in dimethylsulphoxide (25 ml) added dropwise. The temperature was kept between 20°–25° C by external cooling. The mixture was stirred for half an hour at room temperature and quenched into ice water (300 ml). It was then carefully acidified to pH 5–6 with cold dilute hydrochloric acid (1:1).

It was extracted into chloroform (3 × 100 ml), the organic layer washed with water (4 × 50 ml), dried over sodium sulphate, filtered and all solvent flash evaporated.

The heavy oil weighed 15 g and slowly crystallised on standing.

Purification was effected by dissolving the thick oil in ethyl acetate (75 ml), charcoal and cooling the filtrate in an ice acetone bath. The white ω-(methylsulfinyl)-3,4,5-trimethyoxyacetophenone was filtered and dried. Wt. = 10 g., m.p. 113°–115° C.

Recrystallised from acetone, the m.p. was 115°–116° C, and the analytical results were: k

|   | Calculated | Found |
|---|---|---|
| C | 53.05 | 52.69 |
| H | 5.92 | 5.84 |

EXAMPLE 104

ω-(Methylsulfinyl) 3,4,5-trimethoxyacetophenone (14 g), desalted water (50 ml) and methanol (35 ml) were combined and cooled to +15° C. With magnetic stirring a solution of sodium borohydride (0.5 g) in water (10 ml) was added. The reaction was exothermic but could be controlled between 15°–20° C with external cooling.

The mixture was stirred at room temperature for 2 hours, and the methanol stripped off by vacuum at 45°–50° C. The aqueous solution was extracted with chloroform (3 × 75 ml), the organic layer washed with water (1 × 75 ml) dried over anhydrous magnesium sulphate, filtered and evaporated to a clear thick oil. A few drops of ethyl acetate caused complete crystallisation β-hydroxy-β-3,4,5-trimethoxyphenethyl methyl sulphoxide. Wt. = 14 g. This was suitable for use in the next step without further purification.

The melting point was 150°–155° C (isomers). Recrystallised from ethyl acetate, the analytical results were:

|   | Calculated | Found |
|---|---|---|
| C | 52.4 | 52.37 |
| H | 6.61 | 6.70 |

EXAMPLE 105

β-Hydroxy-β-3,4,5-trimethoxyphenethyl methyl sulphoxide (5.4 g), β-anilinopropionitrile (3 g), dimethylsulphoxide (25 ml) and sodium methylate (2.0 g) were combined in a flask at room temperature and warmed slowly with stirring, on a steam bath up to 90°–95° C. The mixture became very dark in colour and the reaction was complete in 20 minutes at 95° C.

The mixture was quenched in ice water and dark oily precipitated washed by decantation. It was dissolved in ethanol (15 ml) and cooled. The heavy yellow crystalline precipitate was filtered, washed with cold ethanol and hexane, and dried. Wt. = 2 g. The product was identical with a sample prepared from the 3,4,5-trimethoxybenzaldehyde and β-anilinopropionitrile.

Hexamethylphosphoramide has been substituted for the dimethyl sulphoxide, as well as potassium hydroxide in methanol for the sodium methylate, with the same results in all cases.

EXAMPLE 106

A guanidine solution was prepared from guanidine hydrochloride (15 g), sodium methoxide (10 g) and ethanol (100 ml). It was cooled, filtered salt-free, and combined with α-(3,4,5-trimethoxybenzyl) β-anilinoacrylonitrile (16 g). It was then refluxed on a steam bath overnight, and the hot solution was treated with charcoal Darco G-60 (2.0 g) and evaporated to ¼ volume. It was cooled to complete crystallisation, filtered and washed with cold ethanol, acetone and ether and dried. Wt. = 13 g. (91% theory), m.p. 198°–200° C.

EXAMPLE 107

The procedure of Example 2 was repeated using hexamethylphosphoramide (40 ml) in place of dimethylsulphoxide, and on work-up β-anilino-α-3,4,5-trimethoxybenzylacrylonitrile was obtained. Wt. = 26 g. m.p. 126°–128° C.

EXAMPLE 108

A mixture of (3.3 g; 0.0115 mole) of methyl α-(3,4,5-trimethoxyacetophenone) sulfone, isopropanol (distilled from aluminum isopropoxide) (75 ml) and of aluminum isopropoxide (2.7 g; 0.0132 mole) was heated to reflux. Periodically, a few drops of distillate were taken from beyond a 15 inch Vigreaux column and tested for the presence of acetone with 2,4-dinitrophenyl hydrazone reagent. After two days of refluxing and removal of distillate the acetone test became negative. During the refluxing period additional dry isopropyl alcohol (50 ml) was required to replace that removed for testing. The reaction mixture was evaporated to dryness and mixed with 2N hydrochloric acid (230 ml). The mixture was washed 4 times with chloroform. The combined chloroform washes were dried over magnesium sulfate and evaporated to give a solid, 3.3 g (97%); m.p. 151°–3° C. Recrystallisation from chloroformbenzene gave β-hydroxy-β-3,4,5-trimethoxyphenethylmethylsulfone, 3.1 g. (92%); m.p. 153.5°–155.5° C. The recrystallised product showed one spot on silica gel thin layer after development with chloroform-acetone (9:1) and visualization with iodine vapors.

EXAMPLE 109

β-Hydroxy-β-3,4,5-trimethoxyphenethylmethylsulphone (5 g), β-anilinopropionitrile (3 g) dimethylsulphoxide (20 ml) and a solution of potassium hydroxide in methanol (20%; 2 ml) were reacted together at 90°–95° C for 20 minutes. Work-up gave β-anilino-α-3,4,5-trimethoxybenzylacrylonitrile (3 g) m.p. 126°–129° C (recrystallised from ethanol).

EXAMPLE 110

The procedure of Example 109 was repeated using hexamethylphosphoramide (20 ml) in place of dimethylsulphoxide and on work-up gave β-anilino-α-3,4,5-trimethoxybenzylacrylonitrile (2 g) m.p. 125°–127° C (recrystallised from ethanol).

EXAMPLE 111

The procedure of Example 110 was repeated using sodium methoxide (0.5 g) in place of potassium hydroxide in methanol, and on work-up gave β-anilino-α-3,4,5-trimethoxybenzylacrylonitrile. Wt. = 3 g., m.p. 128°–130° C.

EXAMPLE 112

β-Hydroxy-β-3,4,5-trimethoxyphenethylmethylsulphone (10 g), β-anilinopropionitrile (5.1 g), hexamethylphosphoramide (20 ml), and sodium methoxide (1 g) were reacted at 60° C for 30 minutes, and on work-up gave β-anilino-β-3,4,5-trimethoxybenzylacrylonitrile. Wt. = 6 g., m.p. 127°–129° C.

EXAMPLE 113

The procedure of Example 110 was repeated using N,N-dimethylacetamide (25 ml) in place of dimethylsulphoxide, and on work up gave β-anilino-β-3,4,5-trimethoxybenzylacrylonitrile. Wt. = 2.5 g., m.p. 125°–128° C.

EXAMPLE 114

β-Hydroxy-β-3,4,5-trimethoxyphenethylmethylsulphoxide (5.4 g), β-anilinopropionitrile (3 g), dimethylsulphoxide (25 ml), and sodium methylate (0.5 g) were reacted together at 90°–95° C for one hour. The mixture was then poured into ice-water; the solid collected, and recrystallised from denatured ethanol to give β-anilino-β-3,4,5-trimethoxybenzylacrylonitrile. Wt. = 2 g. (30%) m.p. 125°–127° C.

EXAMPLE 115

The procedure in Example 114 was repeated using potassium hydroxide (2 g) in methanol (5 ml) in place of sodium methoxide, and on work-up gave β-anilino-α-3,4,5-trimethoxybenzylacrylonitrile. Wt. = 2 g., m.p. 125°–128° C.

EXAMPLE 116

The procedure in Example 114 was repeated using hexamethylphosphoramide in place of dimethylsulphoxide and sodium methoxide (2 g), and on work-up gave β-anilino-α-3,4,5-trimethoxybenzylacrylonitrile. Wt. = 2 g., m.p. 125°–129° C.

EXAMPLE 117

The procedure in Example 114 was repeated using potassium t-butoxide in t-butanol (13.6%; 15 ml) in place of sodium methoxide, and on work-up gave β-anilino-α-3,4,5-trimethoxybenzylacrylonitrile. Wt. = 1 g., m.p. 128°–130° C.

EXAMPLE 118

The procedure in Example 117 was repeated using hexamethylphosphoramide (25 ml.) in place of dimethylsulphoxide, and on work-up gave β-anilino-α-3,4,5-trimethoxybenzylacrylonitrile. Wt. = 1 g., m.p. 123°–126° C.

EXAMPLE 119

β-Morpholinopropionitrile (3.0 g), β-hydroxy-β-3,4,5-trimethoxyphenethylmethylsulphone (2.9 g), sodium methoxide (0.3 g) and hexamethylphosphoramide (6 ml) were reacted together at 60°–65° C for 40 minutes, and then poured into ice-water (50 ml). The crude solid was collected by decantation and recrystallised from ethanol (10 ml) to give β-morpholino-α-3,4,5-trimethoxybenzylacrylonitrile. Wt. = 2 g.

EXAMPLE 120

The procedure in Example 118 was repeated using benzyltrimethylammonium hydroxide in place of sodium methoxide and on work-up β-morpholino-α-3,4,5-trimethoxybenzylacrylonitrile was obtained in 50% yield.

EXAMPLE 121

β-Anilino-α-3,4,5-trimethoxybenzylacrylonitrile (32 g) and a solution of guanidine hydrochloride (19 g) and sodium methoxide (13 g) in denatured ethanol (100 ml) were heated under reflux for 2½ hours the solvent (31 ml) was boiled off and the mixture was cooled to ° C. The resulting crystals of 2,4-diamino-5-(3',4',5'-trimethoxybenzyl)pyrimidine were collected and washed with denatured ethanol and acetone. Wt. = 27 g. (94%), m.p. 198°–200° C.

Using methanol in place of denatured ethanol gave 2,4-diamino-5-(3',4',5'-trimethoxybenzyl) pyrimidine in 86% yield after 6 hours reflux; with isopropanol the reaction was over in 2 hours and the yield was 78%.

EXAMPLE 122

The products from Examples 102 (b) to (f), were converted by the procedure of Example 21., into
a. 2,4-Diamino-5-(3',4'-dichlorobenzyl) pyrimidine, m.p. 237°–239°.
b. 2,4-Diamino-5-(2'-iodobenzyl)pyrimidine, m.p. 265°–267°.
c. 2,4-Diamino-5-(3'-iodobenzyl)pyrimidine, m.p. 220.5°–222°.
d. 2,4-Diamino-5-(4'-iodobenzyl)pyrimidine, m.p. 246°–248°.
e. and 2,4-diamino-5-(2'-bromobenzyl)pyrimidine, m.p. 248°–250°.

EXAMPLE 123

β-Morpholino-α-3,4,5-trimethoxybenzylacrylonitrile (32 g), guanidine carbonate (34 g) and dimethylsulphoxide (50 ml) were heated together at 160° C for 1 hour with good stirring. The reaction mixture was cooled and poured into ice-water (200 ml) and gave 2,4-diamino-5-(3',4',5'-trimethoxybenzyl)pyrimidine which was collected and washed with water and acetone. Wt. = 23.6 g. (80%) m.p. 196°–198° C.

EXAMPLE 124

Methyl p-methylbenzoate is converted into 2,4-diamino-5-(p-methylbenzyl)-pyrimidine, m.p. 166°–171° C., by the procedures of Example 102, Example 105, and Example 106.

EXAMPLE 125

Veratric acid is esterified by refluxing in methanol using hydrochloric acid as catalyst. The resulting methyl 3,4-dimethoxybenzoate is converted under the conditions of Example 103 to ω-(methylsulfinyl) 3,4-dimethoxyacetophenone. This is reduced with sodium borohydride under the condition of Example 104 to β-hydroxy-β-(3,4-dimethoxyphenyl)ethyl methyl sulphoxide, which is then allowed to react with β-anilinopropionitrile in hexamethylphosphoramide containing sodium methylate according to Example 105. The resulting α-(3,4-dimethoxybenzyl)-β-anilinoacrylonitrile is condensed with guanidine according to Example 106 to give 2,4-diamino-5-(3',4'-dimethoxybenzyl) pyrimidine, m.p. 224°–229° C.

EXAMPLE 126

2-Ethyl-4,5-dimethoxybenzoic acid is esterified in methanol containing hydrochloric acid. The methyl ester is converted consecutively to methyl-α-(2-ethyl-4,5-dimethoxyacetophenone) sulphone, methyl-β-hydroxy-β-(2-ethyl-4,5-dimethoxyphenyl)ethyl sulphone, and β-anilino-α-(2-ethyl-4,5-dimethoxybenzyl) acrylonitrile according to Example 107. Following the procedure of Example 121 the β-anilino-α-(2-ethyl-4,5-dimethoxybenzyl) acrylonitrile is allowed to react with guanidine to give 2,4-diamino-5-(2'-ethyl-4',5'-dimethoxybenzyl)pyrimidine, m.p. 206°–207° C. after recrystallization from 60% to ethanol.

EXAMPLE 127

Syringic acid was esterified by the Fischer Method using concentrated sulfuric acid as catalyst and a large excess of methanol to give a nearly quantitative yield of methyl syringate, m.p. 104°–106° C. after recrystallization from isopropanol and hexane.

A mixture of 21.2 g. of methyl syringate, 15 g. of potassium carbonate, 1 g. of sodium iodide, 70 ml. of 95% ethanol (5% methanol), and 14 g. of benzyl chloride was heated at reflux with stirring for 4 hours. The alcohol was stripped off, ice water added, and the mixture extracted with ether. The ether exxtract was washed with water and the ether stripped off. Benzene was added and stripped to remove traces of water. The residual oil was dissolved in isopropanol, charcoal added, and the mixture filtered. Hexane was added and the solution cooled. A total of 19 g. (63% yield) of methyl 3,5-dimethoxy-4-benzyloxybenzoate, m.p. 62°–65° C., was obtained.

A mixture of 6 g. of sodamide, 45 ml. of dimethylsulphoxide, and 11.5 g. of dimethylsulphone was heated for 1 hour at 60° C. with stirring and then cooled to 50° C. To this was added 17 g. of methyl 3,5-dimethoxy-4-benzyloxybenzoate. The solution was heated at 60° C. for 1 hour and poured into 200 ml. of ice water which was then acidified to pH 2-3. The white crystalline product was dissolved in 400 ml. of 95% ethanol, charcoaled, and filtered. On cooling 16.5 g. (83% yield) of methyl-α-(3,5'dimethoxy-4-benzyloxy-acetophenone) sulphone, m.p. 143°–144° C., was obtained.

The carbonyl group of this sulphone is reduced to a secondary alcohol with sodium borohydride according to the procudure of Example 102. The resulting β-hydroxy-β-(3,5-dimethoxy-4-benzyloxyphenyl)ethylsulphone is allowed to react with β-morpholinopropionitrile according to the procedure of Example 119 to give β-morpholino-α-(3,5-dimethoxy-4-benzyloxybenzyl)acrylonitrile. The latter reacts with guanidine according to Example 123 to give 2,4-diamino-5-(3',5'-dimethoxy-4'-benzyloxybenzyl)pyrimidine.

EXAMPLE 128

Following the procedure of Example 127 using n-butyl bromide instead of benzyl chloride 2,4-diamino-5-(3',5'-dimethoxy-4'-n-butoxybenzyl)pyrimidine, m.p. 163°–164° C., is prepared.

EXAMPLE 129

3-Bromo-4-methoxybenzoic acid is esterified by the Fischer method and the ester converted successively into methyl-α-(3-bromo-4-methoxyacetophenone) sulphone, β-hydroxy-β-(3-bromo-4-methoxyphenyl)ethyl sulphone, β-anilino-α-(3-bromo-4-methoxybenzyl)acrylonitrile, and 2,4-diamino-5-(3'-bromo-4'-methoxybenzyl) pyrimidine following successively the procedures of Examples 102, 102a, and 106. The pyrimidine has a m.p. of 232°–233° C.

EXAMPLE 130 a. 2,4,6-trimethylmethyl benzoate is converted into 2,4-diamino-5-(2',4',6'-trimethylbenzyl)pyrimidine by the procedure of examples 102, 105 and 106.

b. 2-bromo-3,4,5 trimethoxymethyl benzoate is converted into 2,4-diamino-5-(2'-bromo-3',4',5'-trimethoxybenzyl)pyrimidine by the procedure of examples 102, 105 and 106.

c. 2-bromo-3,5-dimethoxy-4n butoxy methyl benzoate is converted into 2,4-diamino-5-(2'-bromo-3',5-dimethoxy-4'-n-butoxybenzyl)pyrimidine by the procedure of examples 102, 105 and 106.

d. 3,4 methylenedioxy methyl benzoate is converted into 2,4-diamino-5-(3',4'methylenedioxy benzyl)-pyrimidine by the procedure of examples 102, 105 and 106.

EXAMPLE 131

Trimethoprim
2,4-diamino-5-(3',4',5'-trimethoxybenzyl)pyrimidine

Prepare a guanidine solution from 15 gm. guanidine HCl, 10 gm. sodium methylate, and 100 ml. ethanol. Cool, filter salt free, and combine with 16 gm. α(3,4,5-trimethoxy-benzyl)β-anilinoacrylonitrile. Reflux on a steam bath overnight, charcoal the hot solution with 2.0 gm. Darco G-60 and evaporate to ¼ volume. Cool to complete crystallization, filter, and wash with cold ethanol, acetone, and ether. Dry. Weight = 13+gm.~91% theory. M.P. 198°–200° C.

EXAMPLE 132

β-hydroxyβ-3,4,5-trimethoxyphenethylmethylsulphoxide

Sodium methylate (5.4 gm.) was dissolved in hot dimethylsulfoxide (50 ml.), the solution was cooled to room temperature, 3,4,5-trimethoxybenzaldehyde (18 gm.) was added, and the mixture was stirred at room temperature for 2 hours. Water (100 ml.) was then added to the mixture which was next extracted with chloroform. The chloroform extract was washed with water, dried over anhydrous sodium sulfate, and evaporated to dryness. The residual yellow oil crystallized on addition of ethylacetate. The crystals were collected and washed with pentane. Weight = 14.8 gm. (59%) M.P. 160°–162° C (after recrystallization from ethylacetate.) I.R. and U.V. spectra in agreement with structure.

|   | Calculated | Found |
|---|---|---|
| C | 52.4 | 52.37 |
| H | 6.61 | 6.70 |

What is claimed:

1. The method of preparing a compound of formula I

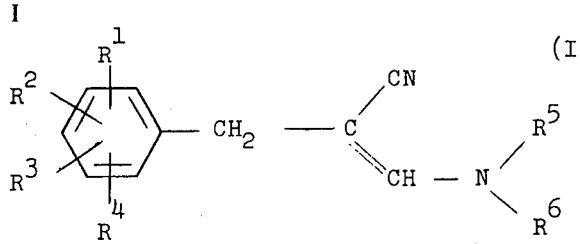

which comprises reacting a compound of formula II

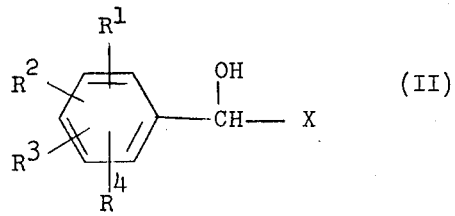

where X is $CH_2SO_2CH_3$ or $CH_2SOCH_3$ with a compound of formula III

in a polar non-aqueous solvent and in the presence of base where the amine $NR^5R^6$ is a primary or secondary amino group of 1 to 12 carbons and $R^1$–$R^4$ are the same or different and each is hydrogen, halogen, lower alkyl, lower alkoxyl, or benzyloxy, or $R^3$ and $R^4$ taken together may be a methylenedioxy group when both $R^1$ and $R^2$ are hydrogen atoms and wherein the lower alkyl and lower alkoxy contain 1 to 4 carbons.

2. The method according to claim 1 where the base is a strong base.

3. The method according to claim 2 in which the base is a methoxide or tertiary butoxide anion and the solvent is dimethylsulphoxide.

4. The method according to claim 3 wherein the reaction is carried out at an elevated temperature above 30° C.

5. The method according to claim 1 wherein compound III is β-anilino-propionitrile.

6. The method according to claim 1 where compound III is β-anilino-propionitrile and X is $CH_2SO_2CH_3$.

7. The method according to claim 1 where compound III is β-anilino-propionitrile and X is $CH_2SOCH_3$.

8. The method according to claim 6 wherein the base is potasium t-butoxide.

9. The method according to claim 7 wherein the base is potassium t-butoxide.

10. The method according to claim 1 in which $R^5$ is hydrogen and where $R^6$ is aryl of 6 to 12 carbons which may be substituted in one, two or three positions with lower alkyl, lower alkoxy or halogen wherein lower alkyl and lower alkoxy contain 1 to 4 carbons.

11. The method according to claim 1 in which the solvent is a polar aprotic solvent.

12. The method according to claim 11 in which the base is a hydroxide, alkoxide or methylsulphinyl carbanion.

13. The method according to claim 1 in which the base is a hydroxide, alkoxide or methyl sulphinyl carbanion.

14. The method according to claim 1 in which the amino group is such that its free amine $HNR^5R^6$ has a pKa from 0 to 6.

15. The method according to claim 1 in which one of $R^1$–$R^4$ is para lower alkoxy.

16. The method according to claim 1 in which one of $R^1$–$R^4$ is para lower alkyl.

17. The method according to claim 1 in which one of $R^1$–$R^4$ is hydrogen and the others are methoxyl at the 3,4 and 5 positions of the ring.

18. The method according to claim 1 in which two of $R^1$–$R^4$ is hydrogen and the others are methoxyl at the 3 and 4 positions of the ring.

19. The method according to claim 1 in which one of $R^1$–$R^4$ is hydrogen, another of $R^1$–$R^4$ is methyl at the 2 position of the ring and the remaining $R^1$–$R^4$ are methoxyl at the 4 and 5 positions of the ring.

20. The method according to claim 1 in which one of $R^1$–$R^4$ is chlorine, bromine or iodine.

21. The method of claim 1 in which β-hydroxy-β-3,4,5-trimethoxyphenethylmethylsulphone is reacted with β-anilinopropionitrile to prepare β-anilino-α-

3,4,5-trimethoxybenzylacrylonitrile.

22. The method of claim 1 in which β-hydroxy-β-3,4,5-trimethoxyphenethylmethylsulphoxide is reacted with β-anilinopropionitrile to preparee β-anilino-α-3,4,5-trimethoxybenzylacrylonitrile.

23. The method of claim 1 in which β-hydoxy-β-3,4,5-trimethoxyphenethylmethylsulphone is reacted with β-morpholinopropionitrile to prepare β-morpholino-α-3,4,5-trimethoxybenzylacrylonitrile.

24. The method of claim 1 in which β-hydroxy-β-(3,4-dichlorophenethyl)methylsulphone is reacted with β-anilinopropionitrile to prepare β-anilino-α-3,4-dichlorobenzylacrylonitrile.

25. The method of claim 1 in which β-hydroxy-β-(2-iodophenethyl) methyl sulphone is reacted with β-anilinopropionitrile to preare β-anilino-α-2-iodobenzylacrylonitrile.

26. The method of claim 1 in which β-hydroxy-β-(3-iodophenethyl) methyl sulphone is reacted with β-anilinopropionitrile to prepare β-anilino-α-3-iodobenzylacrylonitrile.

27. The method of claim 1 in which β-hydroxy-β-(4-iodophenethyl)methyl sulphone is reacted with β-anilinopropionitrile to prepare β-anilino-α-4-iodobenzylacrylonitrile.

28. The method of claim 1 in which β-hydroxy-β-(2-bromophenethyl) methyl sulphone is reacted with β-anilinopropionitrile to prepare β-anilino-α-2-bromobenzylacrylonitrile.

29. The method of claim 1 in which β-hydroxy-β-(3,4,-dimethoxyphenyl)ethylmethylsulphoxide is reacted with β-anilinopropionitrile to prepare α-(3,4-dimethoxybenzyl)-β-anilinoacrylonitrile.

30. The method of claim 1 in which methyl-β-hydroxy-β-(2-ethyl-4,5-dimethoxypheny)ethyl sulphone is reacted with β-anilinopropionitrile to prepare β-anilino-α-(2,ethyl-4,5-dimethoxybenzyl)acrylonitrile.

31. The method of claim 1 in which methyl-α-(3,5-dimethoxy-4-benzyloxyphenyl)ethylsulphone is reacted with β-morpholino-propionitrile to prepare β-morpholino-α-(3,5-dimethoxy-4-benzyloxybenxyl)acrylonitrile.

32. The method of claim 1 in which the compound III is β-morpholino propionitrile.

33. The method of claim 1 in which β-anilinopropionitrile is reacted with β-hydroxy-β-(3-bromo-4-methoxyphenyl)ethylsulphone to prepare β-anilino-α-(3-bromo-4-methoxybenzyl) acrylonitrile.

* * * * *